US009096848B2

(12) United States Patent
Kimmel et al.

(10) Patent No.: US 9,096,848 B2
(45) Date of Patent: Aug. 4, 2015

(54) METHODS AND DEVICES FOR MANIPULATION OF TARGET CELLS USING A COMBINED APPLICATION OF ACOUSTICAL AND OPTICAL RADIATIONS

(71) Applicant: Technion Research & Development Foundation Ltd., Haifa (IL)

(72) Inventors: Eitan Kimmel, Ramat-HaSharon (IL); Shy Shoham, Haifa (IL); Boris Krasovitski, Nesher (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/671,754

(22) Filed: Nov. 8, 2012

(65) Prior Publication Data
US 2013/0122564 A1 May 16, 2013

Related U.S. Application Data

(60) Provisional application No. 61/557,954, filed on Nov. 10, 2011.

(51) Int. Cl.
G01N 33/48 (2006.01)
C12N 13/00 (2006.01)
C12M 1/42 (2006.01)
A61N 7/00 (2006.01)

(52) U.S. Cl.
CPC ............... *C12N 13/00* (2013.01); *C12M 1/42* (2013.01); *C12M 35/04* (2013.01); *A61N 2007/0039* (2013.01); *C12Q 2523/30* (2013.01)

(58) Field of Classification Search
CPC ................................................. C12Q 2523/30
USPC .......................................................... 702/19
See application file for complete search history.

(56) References Cited

U.S. PATENT DOCUMENTS

| 6,484,052 | B1 | 11/2002 | Visuri et al. |
| 7,083,572 | B2 | 8/2006 | Unger et al. |
| 2007/0265560 | A1 | 11/2007 | Soltani et al. |
| 2008/0319375 | A1 | 12/2008 | Hardy |
| 2010/0030076 | A1 | 2/2010 | Vortman et al. |
| 2011/0178441 | A1 | 7/2011 | Tyler |
| 2013/0046213 | A1 | 2/2013 | Kimmel et al. |
| 2013/0079621 | A1 | 3/2013 | Shoham et al. |

FOREIGN PATENT DOCUMENTS

| WO | WO 00/15097 | 3/2000 |
| WO | WO 2010/009141 | 1/2010 |

OTHER PUBLICATIONS

International Search Report and the Written Opinion Dated Sep. 15, 2011 From the International Searching Authority Re: Application No. PCT/IL2011/000360.
International Search Report and the Written Opinion Dated Aug. 22, 2011 From the International Searching Authority Re: Application No. PCT/IL2011/000359.
Ashush et al. "Apoptosis Induction of Human Myeloid Leukemic Cells by Ultrasound Exposure", Cancer Research, 60: 1014-1020, 2000.
Eller et al. "Rectified Diffusion During Nonlinear Pulsations of Cavitation Bubbles", The Journal of the Acoustical Society of America, 37(3): 493-503, Mar. 1963.
Famy et al. "Nucleating Cavitation From Laser-Illuminated Nano-Particles", Acoustics Research Letters Online, ARLO, 6(3): 138-143, Jul. 2005.
Fujishiro et al. "Increased Heating Efficiency of Hyperthermia Using an Ultrasound Contrast Agent: A Phantom Study", International Journal of Hyperthermia, 14(5): 495-502, Sep.-Oct. 1998. Abstract.
Hao et al. "Rectified Heat Transfer Into Translating and Pulsating Vapor Bubbles", Journal of Acoustical Society of America, 112(5/Pt. 1): 1787-1796, Nov. 2002.
Hao et al. "The Dynamics of Vapor Bubbles in Acoustic Pressure Fields", Physics of Fluids, 11(8): 2008-2019, Aug. 1999.
Holt et al. "Measurements of Bubble-Enhanced Heating From Focused, MHz-Frequency Ultrasound in a Tissue-Mimicking Material", Ultrasound in Medicine & Biology, 27(10): 1399-1412, 2001.
Hu "Spherical Model of an Acoustical Wave Generated by Rapid Laser Heating in a Liquid", The Journal of the Acoustical Society of America, 46(3/Pt.2): 728-736, 1969.
Jain et al. "Au Nanoparticles Target Cancer", NanoToday, 20): 18-29, Feb. 2007.
Kimmel "Cavitation Bioeffects", Critical Review in Biomedical Engineering, 34(2): 105-162, 2006.
Krasovitski et al. "Intramembrane Cavitation as a Unifying Mechanism for Ultrasound-Induced Bioeffects", Proc. Natl. Acad. Sci. USA, PNAS Early Edition, p. 1-6, 2011. & Supporting Information, p. 1-4, 2011.
Krasovitski et al. "Modeling Photothermal and Acoustical Induced Microbubble Generation and Growth", Ultrasonics, 47: 90-101, 2007.
Prosperetti et al. "Bubble Dynamics in a Compressible Liquid. Part 1. First-Order Theory", Journal of Fluid Mechanics, 168: 457-478, 1986.
Pustalov et al. "Thermal Processes During the Interaction of Optical Radiation Pulses With Heterogeneous Laminated Biotissues", International Journal of Heat and Mass Transfer, 33(5): 771-783, 1990.

(Continued)

*Primary Examiner* — Jerry Lin

(57) ABSTRACT

A method of applying a nondestructive mechanical force on one or more cells in aqueous environment by inducing heat generated acoustic pressure pulses. The method comprises providing an energy transmission pattern to induce the applying of a desired nondestructive mechanical force on a at least one cell by forming a plurality of heat generated acoustic pressure pulses in an aqueous environment and instructing the radiation of a target area in proximity to the at least one cell in the aqueous environment with light energy according to the energy transmission pattern.

9 Claims, 15 Drawing Sheets
(12 of 15 Drawing Sheet(s) Filed in Color)

(56) References Cited

OTHER PUBLICATIONS

Stride et al. "On the Destruction of Microbubble Ultrasound Contrast Agents", Ultrasound in Medicine & Biology, 29(4): 563-573, 2003.
Wu "Bubble Mediated Focused Ultrasound: Nucleation, Cavitation Dynamics and Lesion Prediction", Dissertation, Submitted in Partial Fulfillment of the Requirements for the Degree of Doctor of Philosophy, Boston University, College of Engineering, 227 P., 2007.
Zharov "Photothermal Nanotherapeutics and Nanodiagnostics for Selective Killing of Bacteria Targeted With Gold Nanoparticles", Biophysical Journal, 90: 619-627, Jan. 2006.
International Preliminary Report on Patentability Dated Nov. 15, 2012 From the International Bureau of WIPO Re. Application No. PCT/IL2011/000360.
Price et al. "Contrast Ultrasound Targeted Drug and Gene Delivery: An Update on a New Therapeutic Modality", Journal of Cardiovascular Pharmacology and Therapeutics, 7: 171-180, 2002.
Communication Pursuant to Article 94(3) EPC Dated Nov. 15, 2013 From the European Patent Office Re. Application No. 11735701.2.
International Preliminary Report on Patentability Dated Nov. 15, 2012 From the International Bureau of WIPO Re. Application No. PCT/IL2011/000359.
Summons to Attend Oral Proceedings Pursuant to Rule 115(1) EPC Dated Jun. 23, 2014 From the European Patent Office Re. Application No. 11735701.2.
Communication Under Rule 71(3) EPC Dated Nov. 5, 2014 From the European Patent Office Re. Application No. 11735701.2.
Restriction Official Action Dated Dec. 11, 2014 From the US Patent and Trademark Office Re. U.S. Appl. No. 13/696,098.
Official Action Dated Apr. 2, 2015 From the US Patent and Trademark Office Re. Application No. 13/696,098.
Fyrillas et al. "Dissolution or Growth of Soluble Spherical Oscillating Bubbles", Journal of Fluid Mechanics, 277: 381-407, 1994.
Lavon et al., "Bubble Growth Within the Skin by Rectified Diffusion Might Play A Significant Role in Sonophoresis", Journal of Controlled Release, 117: 246-255, Available Online Nov. 6, 2006.

METHODS AND DEVICES FOR MANIPULATION OF TARGET CELLS USING A COMBINED APPLICATION OF ACOUSTICAL AND OPTICAL RADIATIONS

RELATED APPLICATIONS

This application claims the benefit of priority under 35 USC §119(e) of U.S. Provisional Patent Application No. 61/557,954 filed on Nov. 10, 2011.

This application incorporates by reference International Patent Application Nos. PCT/IL2011/000359 and PCT/IL2011/000360, both filed on May 5, 2011.

The contents of the above applications are all incorporated by reference as if fully set forth herein in their entirety.

FIELD AND BACKGROUND OF THE INVENTION

Ultrasound creates a variety of non-thermal effects on biological tissues ranging from necrotic damage to delicate reversible effects like permeability enhancement and excitable tissue stimulation. The present invention, in some embodiments thereof, relates to cell manipulation and, more particularly, but not exclusively, to devices and methods of manipulating cells by generating pressure wave(s in proximity thereto. In a recent study by Krasovitski et al. (2011) a novel mechanism of ultrasound induced intra membrane cavitation is suggested as the reason for ultrasound induced bioeffects in cells, tissue and organ. This mechanism denoted also as Sonophore or Bilayer Sonophore (BLS) suggests that US preferably induces bubble formation in the intra-membrane space between the two lipid leaflets.

The presence of a gas microbubble near the BLS acts as a pressure amplitude amplifier under ultrasound. It is evident today that the ability to introduce microbubbles in the human body is becoming crucial. When subjected to ultrasound, synthetic microbubbles can be used for a variety of therapeutic and diagnostic purposes. Microbubbles can be generated in the body by high intensity ultrasound or introduced intravenously as encapsulated bubbles also known as ultrasound contrast agents (UCA). In-vivo generated microbubbles may improve and widen numerous diagnostic and therapeutic applications in which UCA are currently used. Some of these applications are reviewed by E. Kimmel, Cavitation bioeffects, Critical Reviews in Biomedical Engineering 34 (2006) 105-62, which is incorporated herein by reference. One may also consider ultrasonically induced drug delivery which is based on releasing medication from broken UCAs at a specified location as described in E. Stride, N. Saffari. On the destruction of microbubble ultrasound contrast agents. Ultrasound Med. Biol. 29 (2003) 563-73, which is incorporated herein by reference to and increasing permeability of blood vessel walls for facilitated transport, which is incorporated herein by reference. Also, microbubbles are essential in ultrasonically induced targeted hyperthermia, and diagnostic imaging of specific cells, as well as for increasing membrane permeability of cells for, for instance, gene transfection, see for example R. G. Holt, R. A. Roy. Measurements of bubble-enhanced heating from focused, MHz-frequency ultrasound in a tissue-mimicking material. Ultrasound Med. Biol. 27 (2001) 1399-412, H. Ashush, L. A. Rozenszajn, M. Blass, M. Barda-Saad, D. Azimov, J. Radnay, D. Zipori, U. Rosenschein. Apoptosis induction of human myeloid leukemic cells by ultrasound exposure. Cancer Res. 60 (2000) 1014-20, and R. J. Price, S. Kaul. Contrast ultrasound targeted drug and gene delivery: an update on a new therapeutic modality. J. Cardiovasc. Pharmacol. Ther. 7 (2002) 171-80, which are incorporated herein by reference.

High Intensity Focused Ultrasound (HIFU) sources provide enough power density to initiate bubble generation and growth in-vivo. An HIFU focal pressure of 4.5 MPa produces detectable bubbles in-vivo, see C. H. Farny, T. Wu, G. Holt, T. W. Murray, R. A. Roy. Nucleating cavitation from laser-illuminated nano-particles. Acoust. Res. Let. Online 6 (2005), which is incorporated herein by reference and referred to herein as Farny (2005). For example, S. D. Sokka, R. King, K. Hynynen. MRI-guided gas bubble enhanced ultrasound heating in vivo rabbit thigh. Phys. Med. Biol. 48 (2003) 223-241, which is incorporated herein by reference, suggests the use of very high intensity ultrasound (about 7 kW/cm$^2$ at the focal point) of brief duration (0.5 s) to generate nucleation sites. These are then evolved into microbubbles by application of much lower intensity (about 0.2 kW/cm$^2$) insonification.

An alternative method for generating nucleation sites by exposing light-absorbing gold nanoparticles to laser was suggested by Farny (2005). Gold spherical nanoparticles as well as carbon nano tubes can serve as light-absorbing elements in-vivo because they are biocompatible, conductive and have certain geometrical characteristics that allow them to effectively transform light energy into heat (see Jain et al., see P. K. Jain, I. H. El-Sayed, M. A. El-Sayed. Au nanoparticles target cancer. Nano Today 2 (2007) 18-29, which is incorporated herein by reference. Farny (2005) demonstrated that nanobubbles of about 150 nm in diameter can be obtained by exposing gold nanoparticles embedded in gel to a 532 nm (peak absorption of near-spherical nanoparticles) laser pulse phase-synchronized with an ultrasound burst of 10 cycles, lasting about 10 μs at a frequency of 1.1 MHz. The acoustic pressure amplitude used was 0.9 MPa—namely 20 W/cm$^2$ in a propagating wave. Farny (2005) identified the threshold at which a nanobubble, once generated by a laser pulse heating an individual nanoparticle, evolves into a microbubble. The threshold occurs at acoustic pressures near 1 MPa, for laser energy densities of about 5 mJ/cm$^2$.

V. P. Zharov, K. E. Mercer, E. N. Galitovskaya, M. S. Smeltzer. Photothermalnanotherapeutics and nano diagnostics for selective killing of bacteria targeted with gold nanoparticles. Biophys. J. BioFast, Oct. 20, 2005, doi:10.1529/biophysj.105.061895, which is incorporated herein by reference, demonstrated that exposing bacteria-attached clusters of gold nanoparticles to 532 nm laser pulse-generated nuclei that evolve into microbubbles at laser energy densities above 100 mJ/cm$^2$. Regarding the use of microbubbles for tissue heating, it has been indicated that microbubble oscillations can enhance local ultrasound energy deposition by two orders of magnitude, see S. Fujishiro, M. Mitsumori, Y. Nishimura, Y. Okuno, Y. Nagata, M. Hiraoka, T. Sano, T. Marume, and N. Takayama. Increased heating efficiency of hyperthermia using an ultrasound contrast agent: A phantom study. Int. J. Hyperthermia 14 (1998) 495-502, which is incorporated herein by reference.

SUMMARY OF THE INVENTION

According to some embodiments of the present invention, there is provided a method of applying a nondestructive mechanical force on one or more cells in aqueous environment by inducing heat generated acoustic pressure pulses, comprising: providing an energy transmission pattern to apply a desired nondestructive mechanical force on a at least one cell in an aqueous environment and synchronizing the radiation of a target area in proximity to the at least one cell in the aqueous environment with ultrasound energy and light energy according to the energy transmission pattern.

Optionally, the target area in an intrabody target area.

Optionally, the synchronizing comprises synchronizing the radiation of the target area with the ultrasound energy and the light energy with an estimated oscillation pattern of a cell membrane of the at least one cell.

Optionally, the synchronizing increases the oscillation amplitude of the cell membrane of the at least one cell in relation to an oscillation amplitude caused by a radiation of the light energy according to the energy transmission pattern without the ultrasound energy.

Optionally, the method comprises placing at least one chromophore in the target area.

More optionally, the at least one chromophore comprises at least one nanoparticle.

More optionally, the at least one chromophore comprises at least one red blood cell.

More optionally, the at least one chromophore comprises at least one liposome.

More optionally, the synchronizing comprises evaporating liquid in the aqueous environment around the at least one chromophore to form at least one vapor bubble therearound.

Optionally, the synchronizing comprises forming a shock wave in the target area.

Optionally, the synchronizing comprises forming a pressure pulse as an outcome of rapid thermal expansion without forming a vapor bubble.

According to some embodiments of the present invention, there is provided a system of applying a nondestructive mechanical force on one or more cells in aqueous environment by inducing heat generated acoustic pressure pulses. The system comprises a computing unit or a memory which provides an energy transmission pattern and an interface which synchronizes the radiating of a target area in an aqueous environment with ultrasound radiation and focused light radiation according to the energy transmission pattern to form at least one heat generated acoustic pressure pulse that applies a desired nondestructive mechanical force on at least one cell in proximity to said target area.

According to some embodiments of the present invention, there is provided a method of applying a nondestructive mechanical force on one or more cells in aqueous environment by inducing heat generated acoustic pressure pulses. The method comprises providing an energy transmission pattern to apply a desired nondestructive mechanical force on at least one cell, radiating a plurality of red blood cells in an intrabody target area in proximity to the at least one cell according to the energy transmission pattern to induce a pressure pulse as an outcome of rapid thermal expansion therearound.

Optionally, the radiating comprises synchronizing the radiation of the intrabody target area with ultrasound energy and light energy according to the energy transmission pattern.

According to some embodiments of the present invention, there is provided a method of applying a nondestructive mechanical force on one or more cells in aqueous environment by inducing heat generated acoustic pressure pulses. The method comprises providing an energy transmission pattern to apply a desired nondestructive mechanical force on at least one cell and radiating a plurality of liposomes in an intrabody target area in proximity to the at least one cell according to the energy transmission pattern to induce a pressure pulse as an outcome of rapid thermal expansion therearound.

Optionally, the radiating comprises synchronizing the radiation of the intrabody target area with ultrasound energy and light energy according to the energy transmission pattern.

According to some embodiments of the present invention, there is provided a computerized method of calculating instructions to at least one energy source. The method comprises receiving a desired nondestructive mechanical force to apply on at least one cell in an aqueous environment in proximity to a target area in the aqueous environment, receiving target information defining at least one characteristic the at least one cell, calculating, using a processor, an energy transmission pattern to apply the desired nondestructive mechanical force by forming an heat generated acoustic pressure pulse in the target area, and outputting instructions to allow at least one ultrasound radiation source and at least one focused light source to radiate the target area according to the energy transmission pattern.

Optionally, the desired nondestructive mechanical force is a desired nondestructive mechanical force to apply on a cell membrane of the at least one cell.

More optionally, the desired nondestructive mechanical force is calculated so as to induce at least one of a periodic inflation and a periodic deflation of an intramembrane space of the cell membrane.

Optionally, the aqueous environment is in a human body tissue.

Optionally, the at least one cell comprises a nerve cell, the desired nondestructive mechanical force is set to trigger a stimulation of the at least one cell.

Optionally, the at least one cell comprises a nerve cell, the desired nondestructive mechanical force is set to suppress a stimulation of the at least one cell.

Optionally, the desired nondestructive mechanical force is to generate superficial blood vessels in a tissue comprising the at least one cell.

Optionally, the desired nondestructive mechanical force is to effect permeability of a membrane of the at least one cell.

Optionally, the target information comprises data pertaining to at least one characteristic of at least one chromophore in the target area.

Optionally, the calculating is performed according to a heat balance equation calculated for at least one chromophore in the target area.

Optionally, the wavelength of light emitted by the at least one focused light source is adapted to the light absorption wavelength of at least one chromophore in the target area.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a flowchart of a method for applying nondestructive mechanical force on one or more target cells by inducing heat generated acoustic pressure wave(s) in proximity thereto, for example by forming vapor bubbles, optionally around chromophores, such as nanoparticles, according to some embodiments of the present invention;

FIG. 1B is a schematic illustration of a system of applying a nondestructive mechanical force on one or more cells in aqueous environment by inducing heat generated acoustic pressure pulses, according to some embodiments of the present invention;

FIG. 1C is a schematic illustration of a system that uses a high repetition rate light pulses source for applying a nondestructive mechanical force by inducing heat generated acoustic pressure pulses, according to some embodiments of the present invention;

FIGS. 1D and 1E are graphs depicting activation thresholds for exciting cortical neurons by directing light onto chromophores, according to some exemplary embodiments of the present invention;

Figure 2:
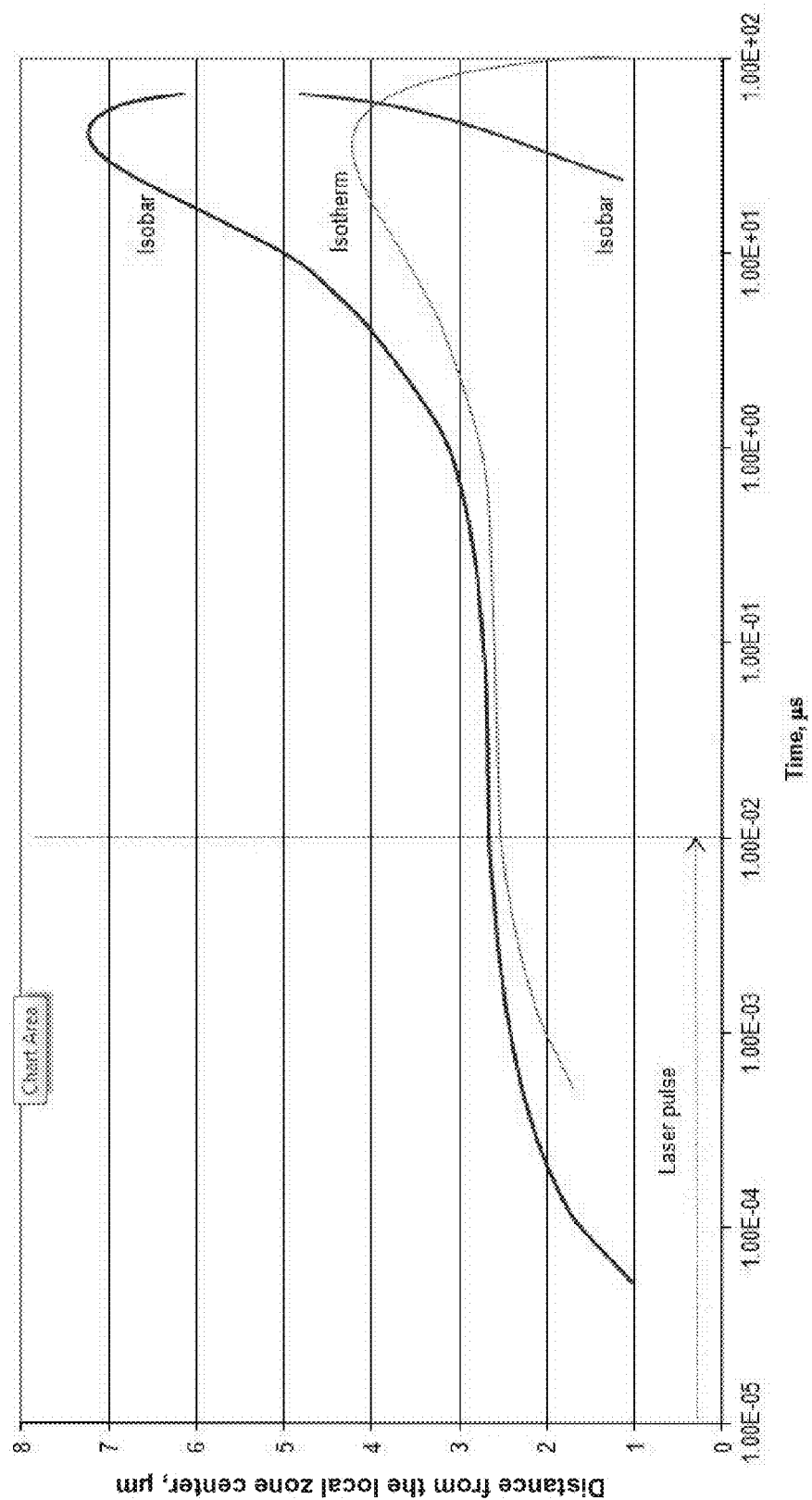
Figure 3:
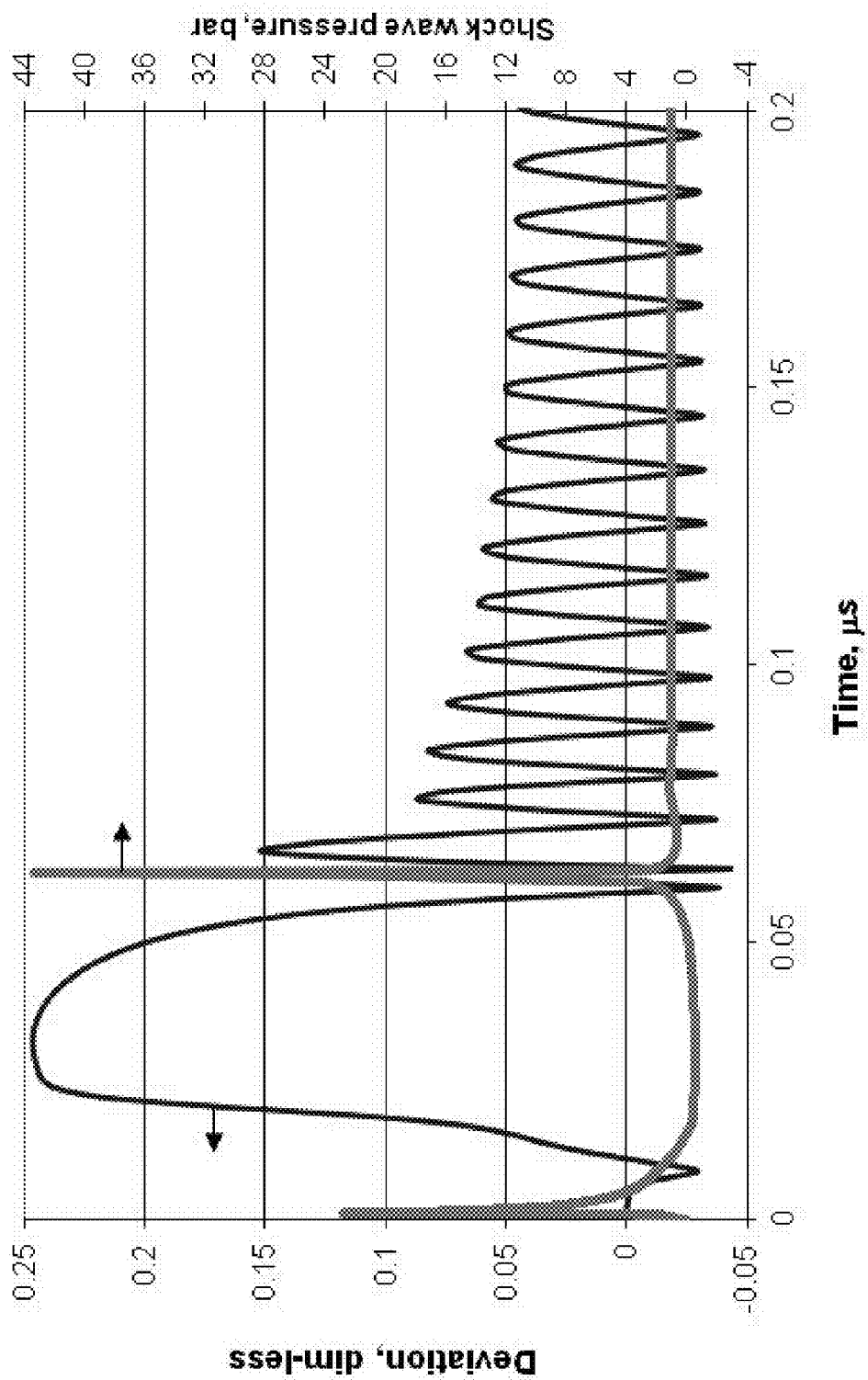
Figure 4:
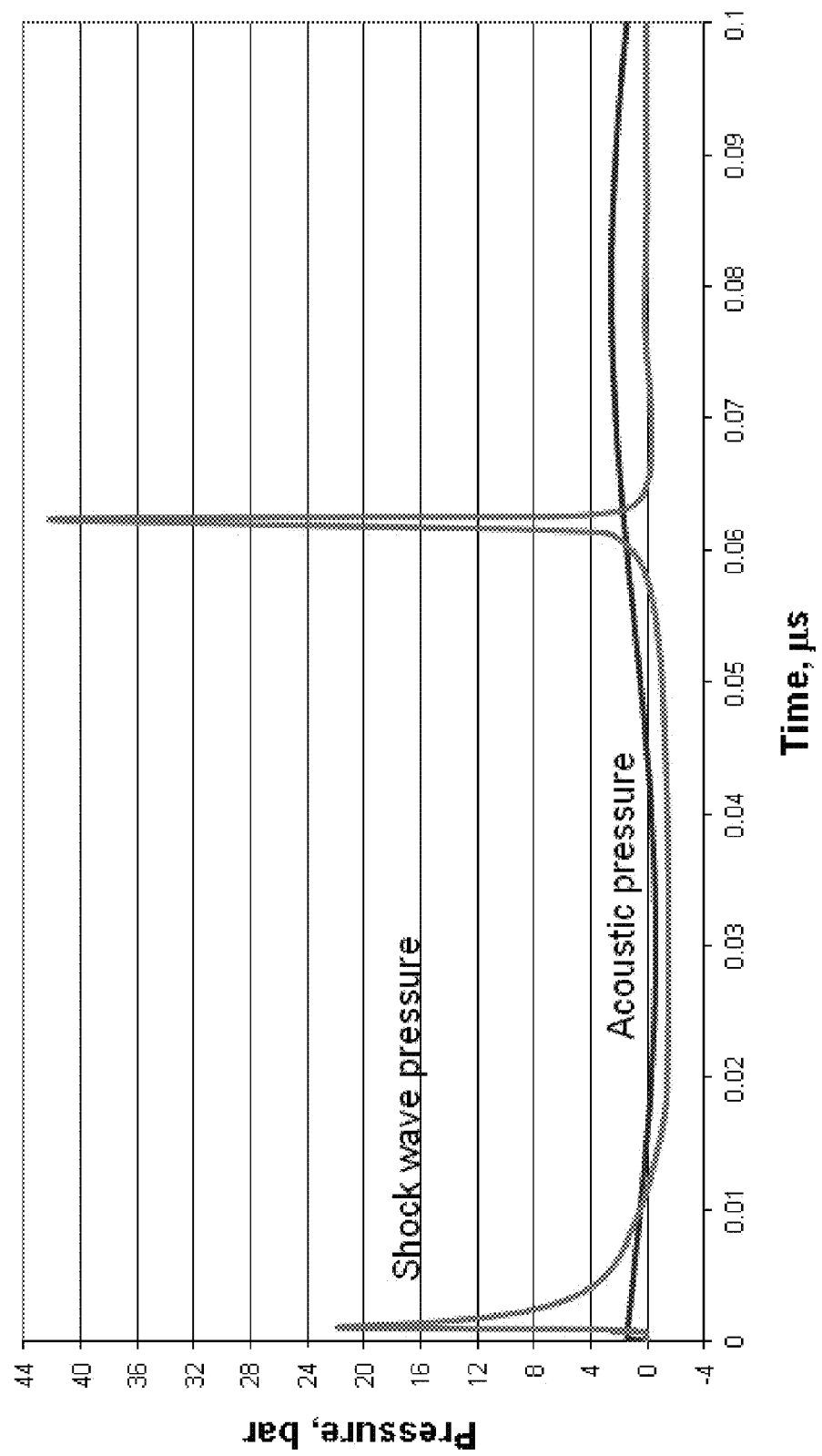
Figure 5:
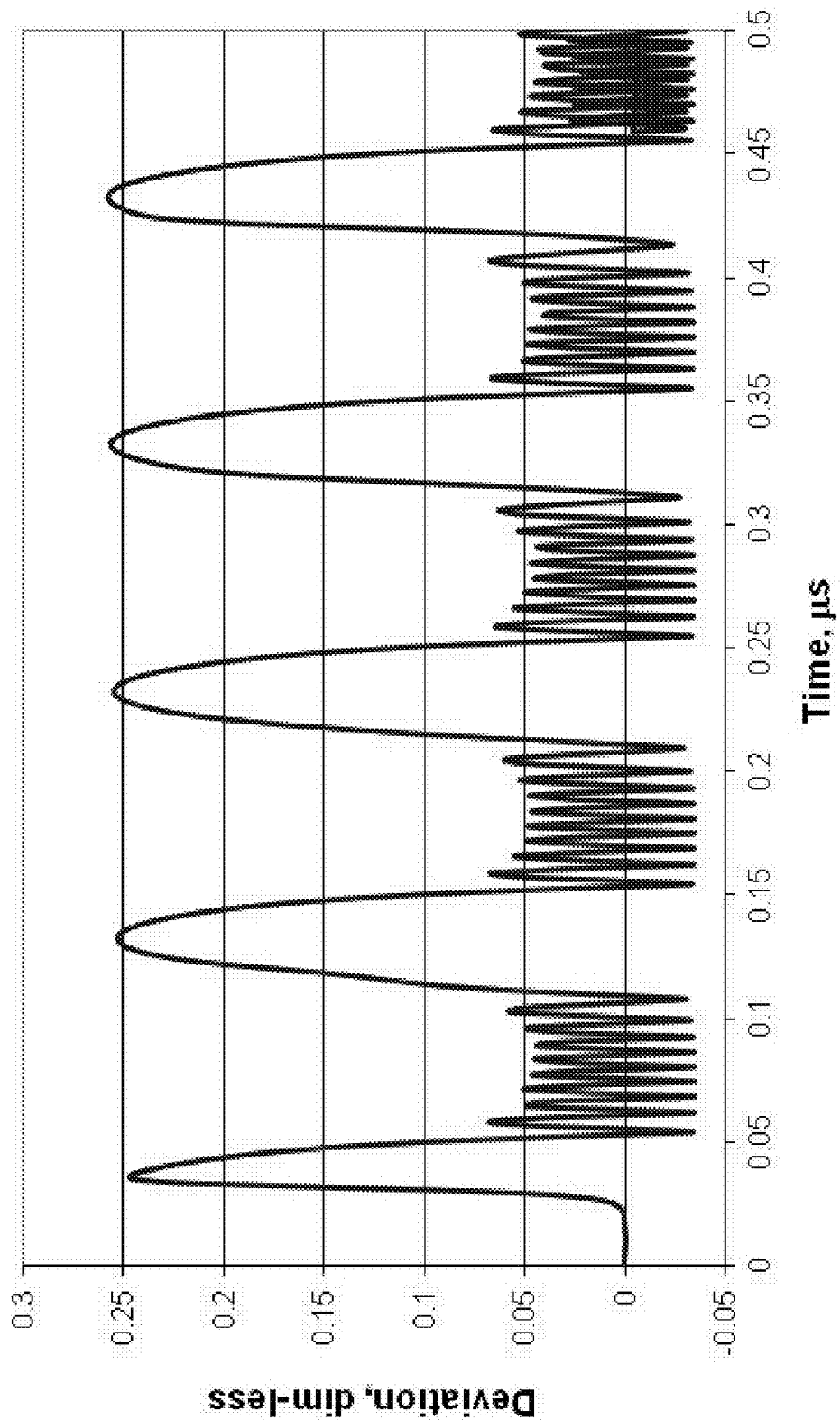
Figure 6:
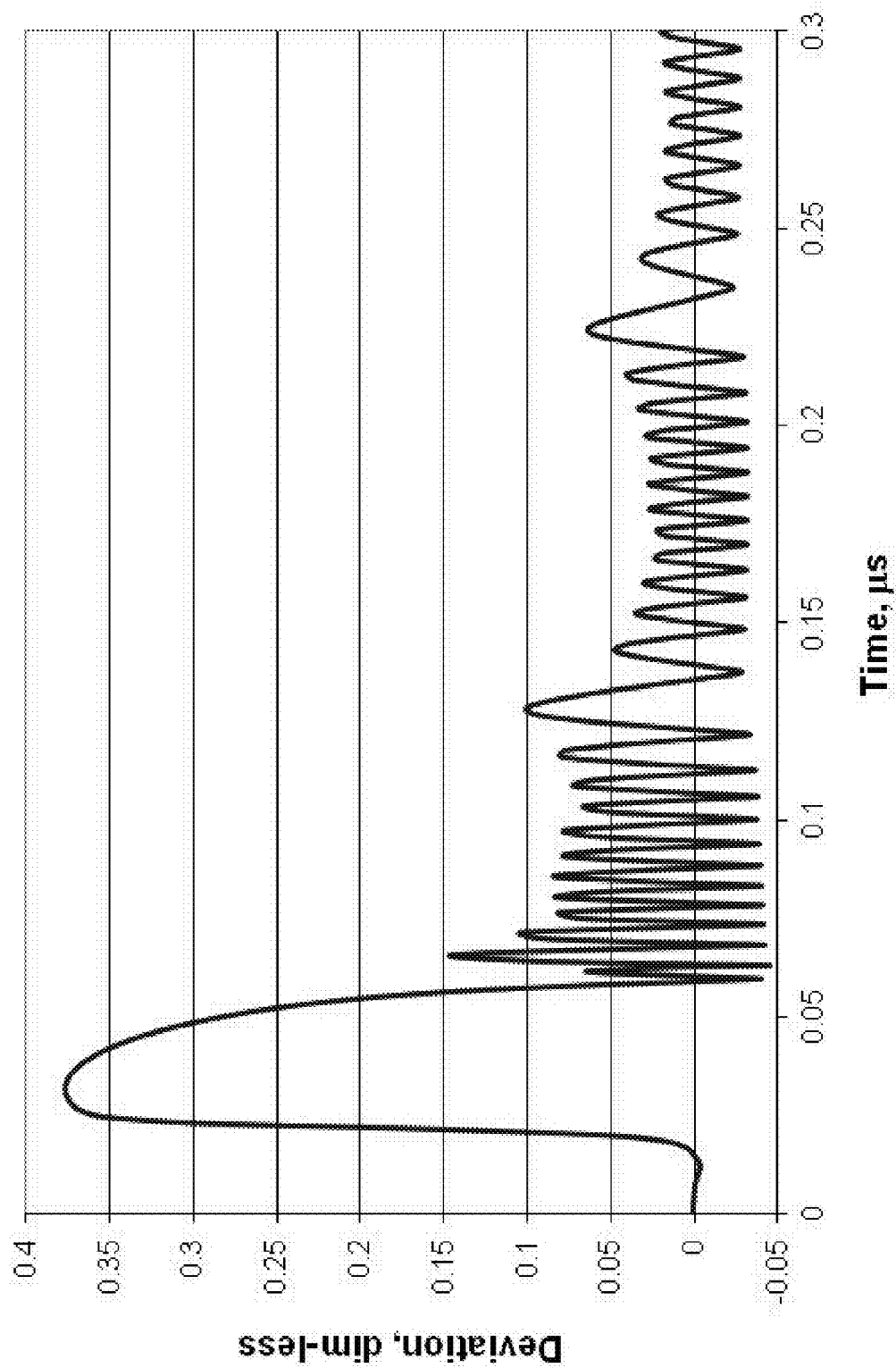
Figure 7A:
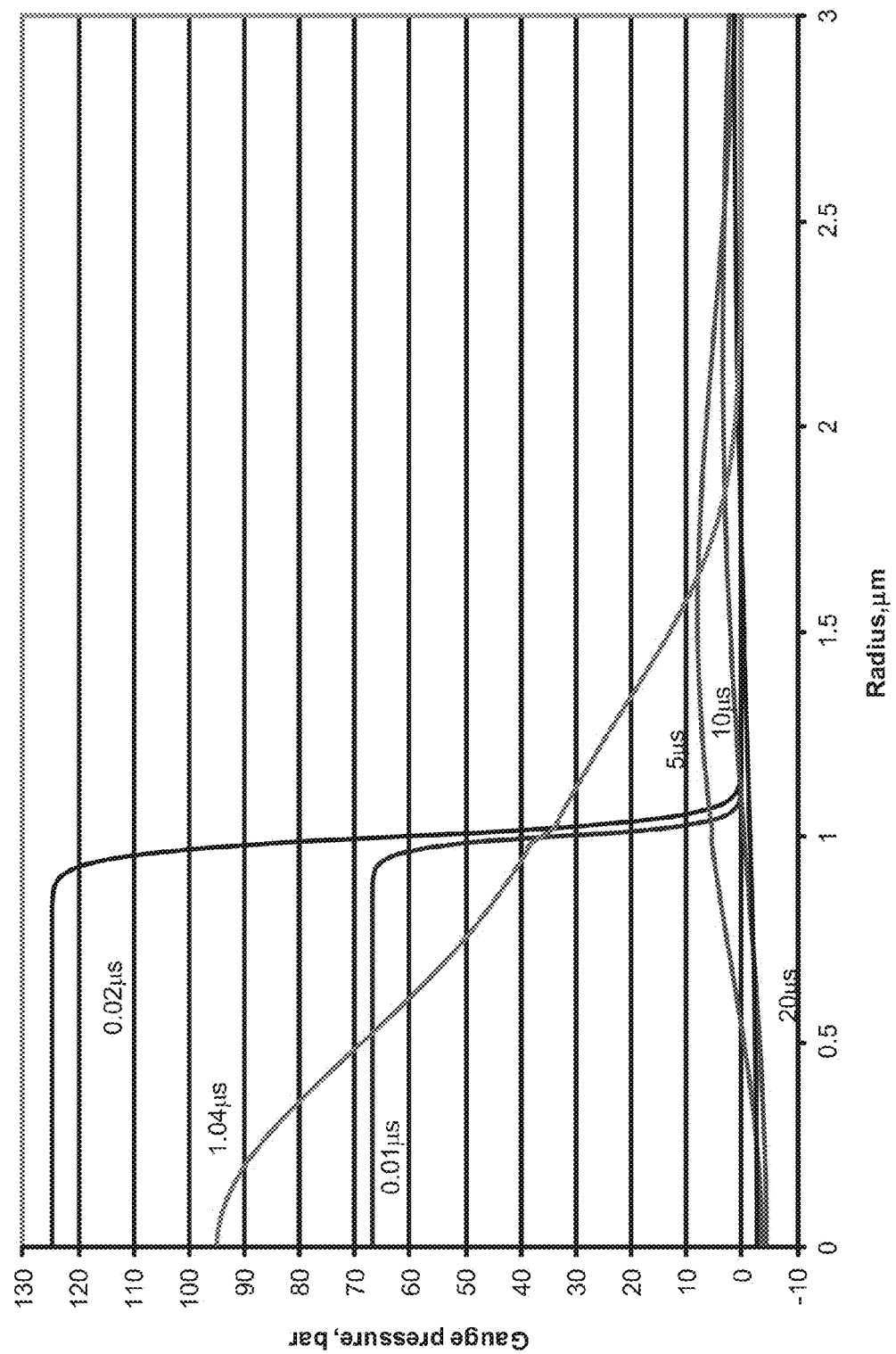
Figure 7B:
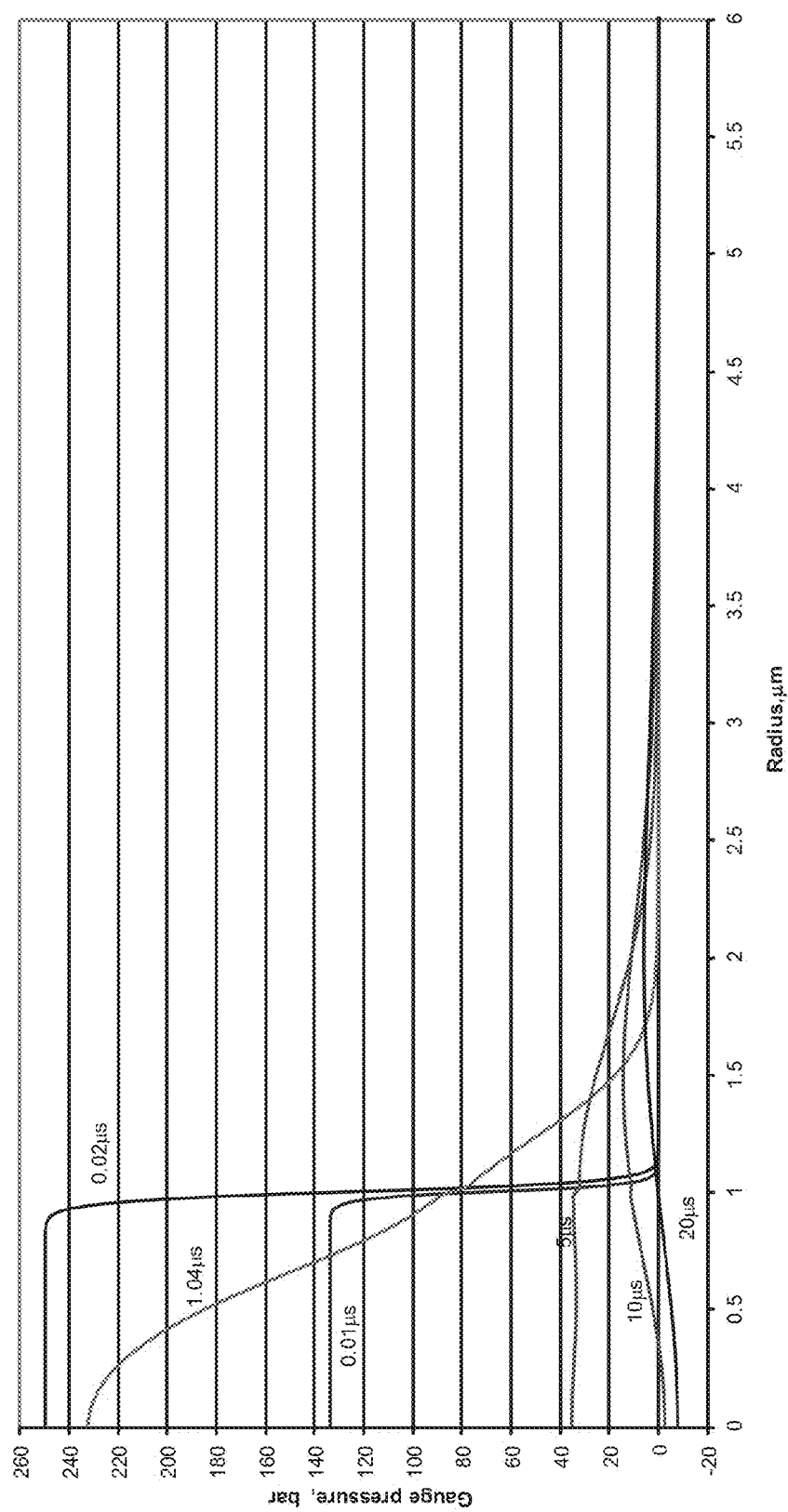
Figure 7C:
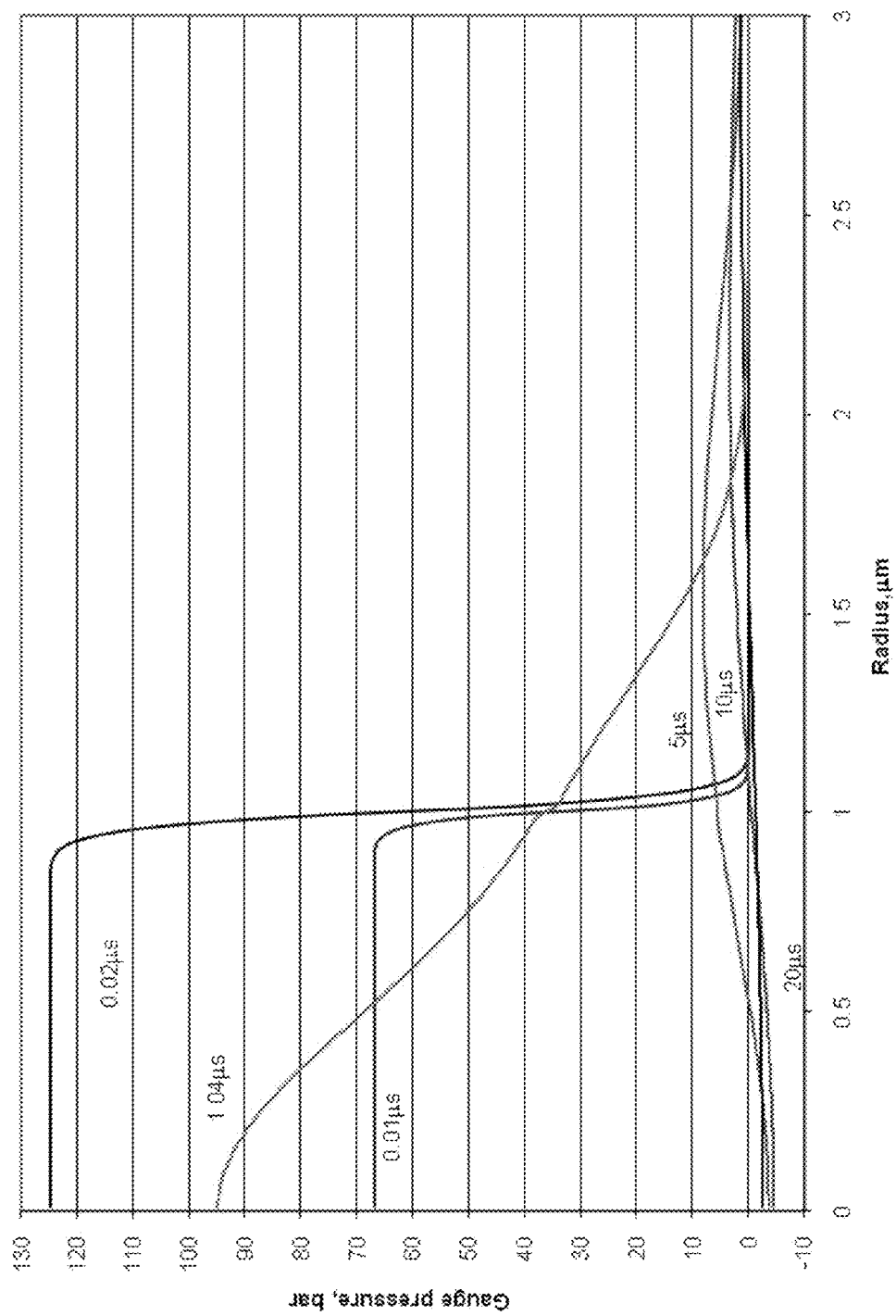
Figure 7D:
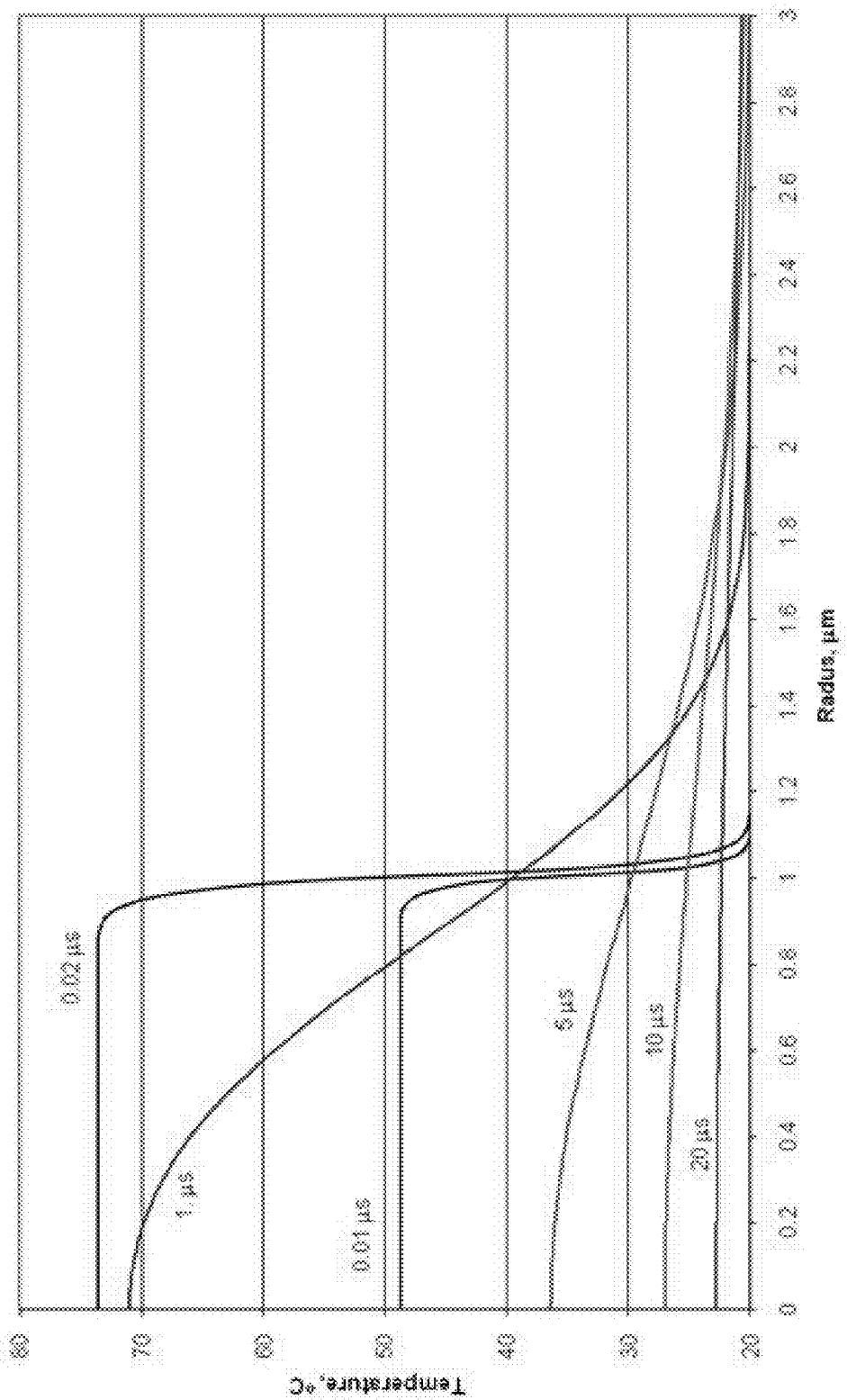
Figure 8:
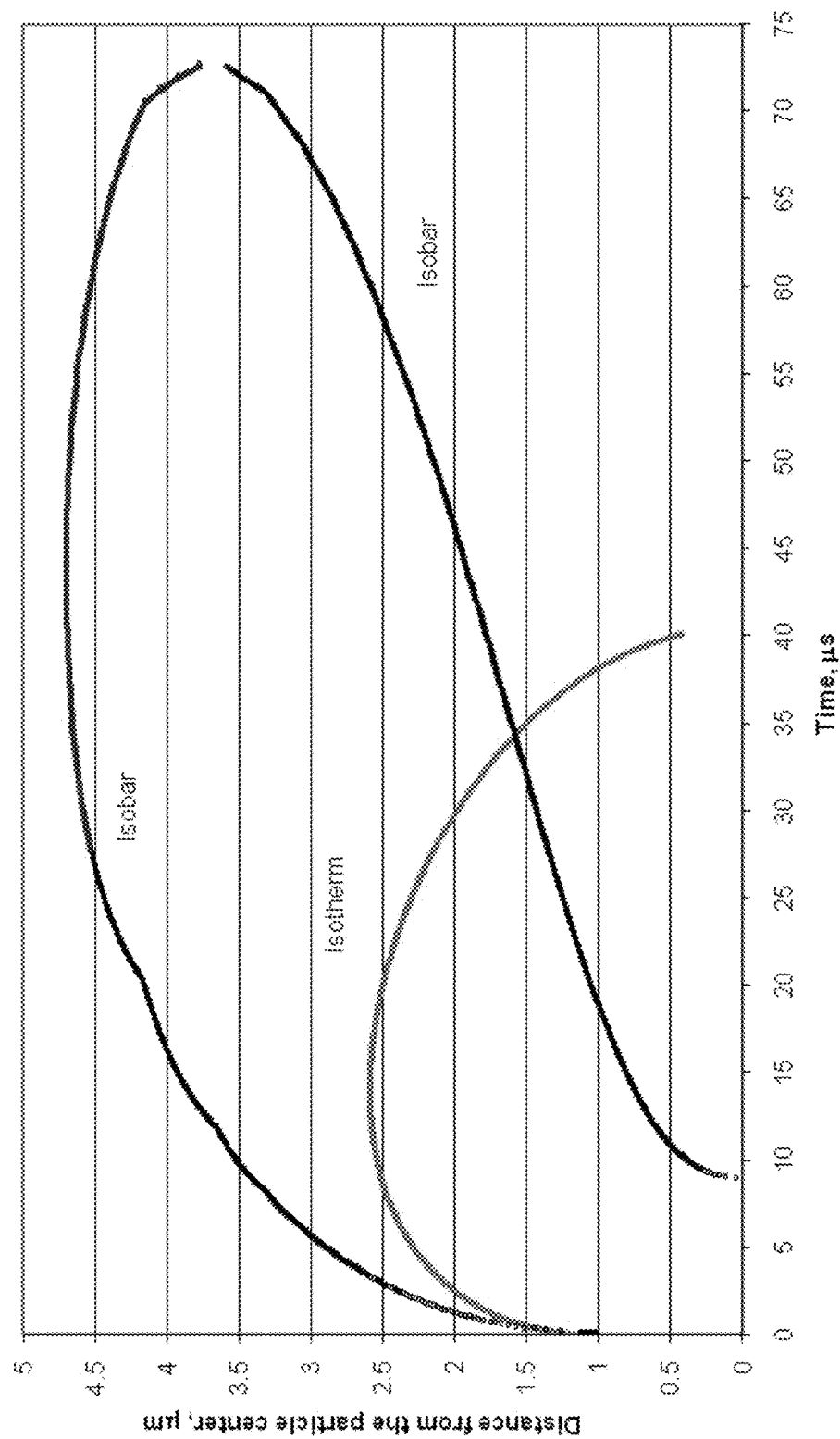
Figure 9:
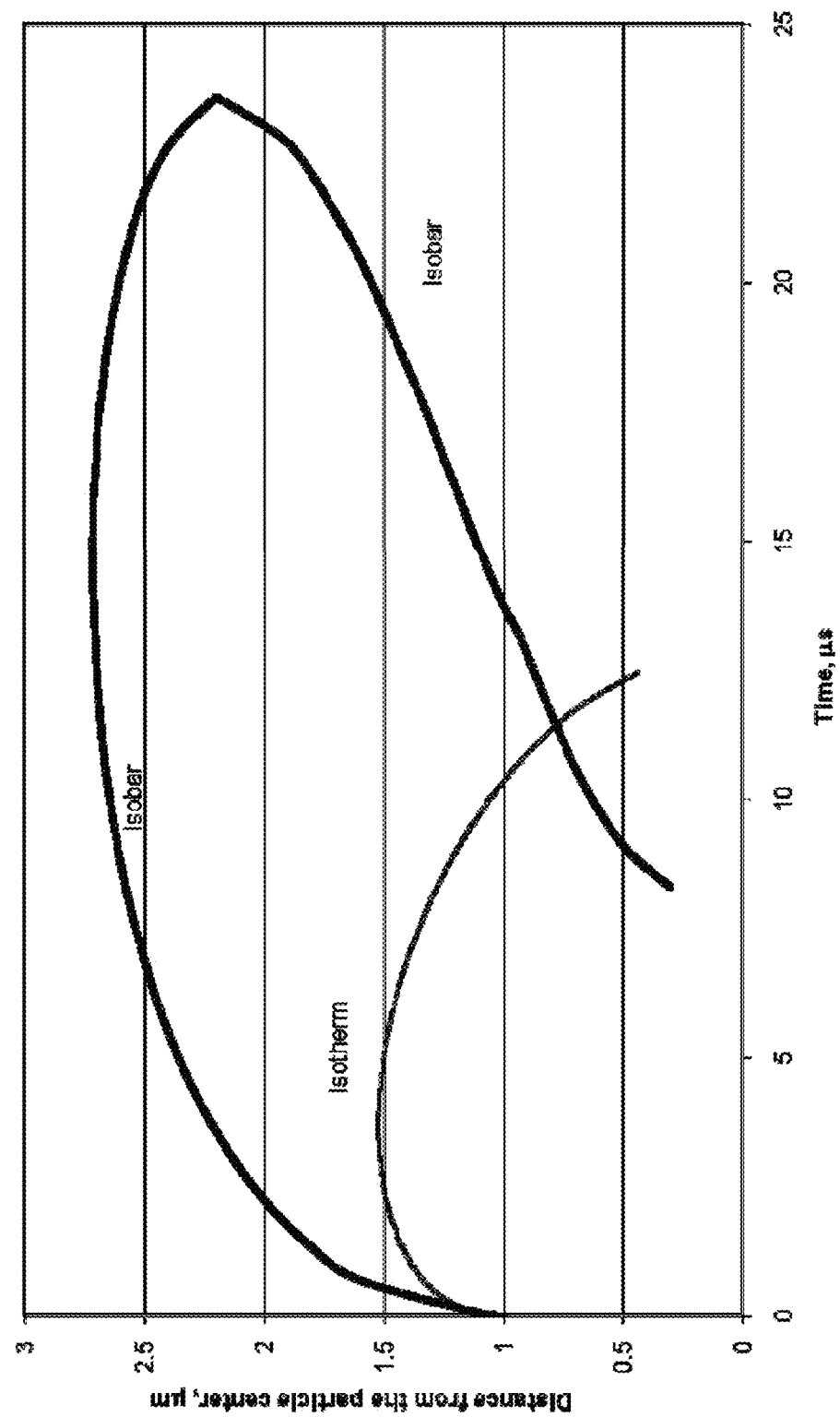

FIG. 2 is an isotherm of the temperature of a target area (1° C. over initial temperature) and isobars of a desired mechanical pressure (1 bar gauge) induced by heat generated acoustic pressure waves as a function of the distance of a chromophore from the target area and a radiation period where the pulse energy is 4.28 mJ, the pulse duration is 10 ns, and the focal laser intensity is 18 kJ/cm$^2$;

FIG. 3 is a graph depicting oscillation of a membrane in response to a shock wave induced by the growing and the collapsing of a vapor bubble around the nanoparticle which is subjected to laser pulse where the membrane diameter is 50 nm, the nanoparticle diameter is 40 nm, and the distance between the particle center and the membrane is 1,000 nm;

FIG. 4 is a graph depicting ultrasound and shock wave pressures on a surface of a membrane affected by ultrasound transmission and a shock wave from a growing and collapsing vapor bubble around nanoparticle subjected to laser pulse where the membrane diameter is 50 nm, the nanoparticle diameter is 40 nm, the distance between the particle center and the membrane is 1,000 nm, the Ultrasound acoustic pressure is 1.6 bar, and the ultrasound frequency is 10 MHz;

FIG. 5 is a graph depicting oscillation of membrane affected by ultrasound where the membrane diameter is 50 nm, the acoustic pressure is 1.6 bar and the ultrasound frequency is 10 MHz;

FIG. 6 is a graph depicting oscillation of membrane affected by ultrasound and shock wave from growing and collapsing vapor bubble around nanoparticle subjected to laser pulse, according to some embodiments of the present invention where the membrane diameter is 50 nm, the nanoparticle diameter is 40 nm, the distance between the particle center and the membrane is 1,000 nm, the ultrasound acoustic pressure is 1.6 bar, and the ultrasound frequency is 10 MHz;

FIGS. 7A-7B are graphs depicting evolution of the gauge pressure field and temperature around the chromophore (granule), when the Granule diameter is 2 μm, the Pulse duration is 20 ns, the Laser beam intensity is 2.4 MW/cm$^2$, and the absorption efficiency is 0.67, according to some embodiments of the present invention;

FIGS. 7C-7D are graphs depicting evolution of the gauge pressure field and temperature around the granule, when the Granule diameter is 2 μm, the Pulse duration is 20 ns, the Laser beam intensity is 2.4 MW/cm$^2$, and the absorption efficiency is 1.33, according to some embodiments of the present invention;

FIG. 8 is a graph depicting an evolution of isobar (1 bar gauge) and isotherm (1° C. over initial temperature) when the granule diameter is 2 μm, the pulse duration is 20 ns, the laser beam intensity is 2.4 MW/cm$^2$ and the absorption efficiency is 1.33; and FIG. 9 is a graph depicting an evolution of isobar (5 bar gauge) and isotherm (5° C. over initial temperature), when the granule diameter is diameter 2 μm, the pulse duration is 20 ns, the laser beam intensity is 2.4 MW/cm$^2$, and the absorption efficiency is 1.33.

DESCRIPTION OF EMBODIMENTS OF THE INVENTION

The present invention, in some embodiments thereof, relates to cell membrane manipulation and, more particularly, but not exclusively, to devices and methods of manipulating cell membranes by inducing heat generated acoustic pressure wave(s) in proximity thereto.

According to some embodiments of the present invention, there are provided targeted and relatively rapid systems and methods for reversible non destructive mechanical manipulation of individual cells, for example activation of excitable cells such as neurons, using a combined, synergistic action of light and ultrasound that create localized pressure pulse(s). These optoacoustic pulses are required to manipulate the cell, for example, through activation of its membranes (BLSs). The high spatial resolution (micrometer-scale) as well as high temporal resolution (sub-millisecond) of the pressure pulses allows manipulating one or few target cells in a tissue without effecting surrounding cells.

By combining light and ultrasound a mechanical force is applied on the target cell(s) without exposing them to high intensities of light radiation or waiving the high level of optical resolution, which is typically several orders of magnitude better than acoustic resolution.

Optionally, the pressure pulse(s) are created by microbubble formation from opto-acoustic heating of chromophore(s), such as clusters of nanoparticles microparticles, which are placed near the target cell(s), in a safely distance therefrom. The heating is optionally performed by a combined action of a modulated, focused laser beam synchronized with an ultrasound beam. The heated chromophore(s) boils the surrounding water to form a microbubble. Upon the rapid expansion and contraction of the microbubble a pressure pulse is generated at a close vicinity to the microbubble. The laser pulse is synchronized with the ultrasonic pressure pulse and thus the bubble formation and optionally the initial detachment of bilayer membranes in the close vicinity enable to manipulate reversibly the cells with minimal laser and ultrasonic intensity. The combination of ultrasonic and laser allows reducing the intensities thereof so that no damage is caused to the target cell(s) and/or the surrounding tissue(s). The controlled pressure pulse is large enough to activate the cell and yet not too large to cause any irreversible damage to the cell. Moreover, the combination of ultrasonic and laser allows reducing the intensities thereof below regulatory thresholds and allow increasing the frequency of the ultrasonic radiation. As further described below, the temperature rise is as minimal as possible. Regarding the BLS and its response to the pressure pulse, microbubbles are generated by pulling away the two leaflets while dissolved gas is accumulating in the hydrophobic zone, creating pockets of gas. Stretching of the leaflets that follows the pocket formation was predicted to initiate mechanotransduction processes in the cell; induce pore formation in the membrane and permeability changes, affect mechano-sensitive ion channels, induce polarization in the membrane of excitable cells and affects voltage sensitive ion channels as well. Greater acoustic pressure open passages in the membrane and may induce rupture of membrane proteins in some cases and rupture of the membrane in others. As to excitable cell manipulation, ultrasound of low intensity can activate neuron circuits both in vitro and in vivo. The pressure amplitudes which are produced at the neuron membrane level were sufficient to activate the neurons and produce action potentials and subsequent calcium influx into the cells. In the embodiments described below, a high resolution is sought for better spatial resolution; for instance when one wants to stimulate an individual cell or a small group of cells.

The opto-acoustic heating of chromophore(s) stimulates cells in a nondestructive way so that the cells in the target zone are stimulated while cells which are not in the target zone are not stimulated. Note that three levels of pressure amplitudes that are tightly connected to the frequency and mechanical index (MI) of the related organ/tissue. Very high pressure amplitude of few megapascal (MPa) is destructive to the cells; medium level of a couple of hundreds of kilopascals (kPa) can activate the BLS and stimulates cells nondestructively; and lower pressure amplitudes that do not affect the cells at all. Having those three regimes in mind (destructive, stimulating but nondestructive and "no effect at all"), the opto-acoustic heating which is described herein generates pressure pulses of amplitudes at the target cells that are below the MI threshold for causing damage and as such are nondestructive (depend on the frequency through the MI definition); but still pressure pulses large enough to activate or stimulate the target cells for e.g. producing action potential in nerve cells or muscle cells. At the same time, all the non target cells which are far from the nanoparticle or the chromophore illuminated by the focused light, and do not sense the every localized effect of the laser pulse heating will not be activated and will stay at their natural/neutral state. This way, optical resolution, which is typically several orders of magnitude better than acoustic resolution, is achieved.

According to some embodiments of the present invention, the chromophore(s) which are used for microbubble formation are red blood cells (RBCs). The microbubble formation is an outcome of the periodic inflation of the intramembrane space around the RBCs, for example in capillaries near the target cells whereas focused light source or laser beam with wavelength that is typically absorbed more in the hemoglobin of the RBCs causes a slight temperature rise in the RBCs and increases their tendency to develop a gas envelope therearound under the combined action of a focused heating source and ultrasound. It should be noted that ultrasound and light radiation may be generated by single sources or distributed sources, for example phased arrays or spatialized modulators.

According to some embodiments of the present invention, the chromophore(s) which are used for microbubble formation are heat sensitive liposomes. The bubble generation is triggered as for RBCs. The liposomes are placed at a safe distance of few micrometers from the target cells. Liposomes can be targeted to attach to the target cells using ligands.

According to some embodiments of the present invention, there are provided methods and systems of calculating instructions to one or more energy sources, for example ultrasound sources and focused light sources. The instructions are set in a manner that the radiation of the target area forms pressure waves, optionally optoacoustic, that apply a desired nondestructive mechanical force on the membrane of one or more cells in an aqueous environment, for example an intrabody tissue. This desired nondestructive mechanical force optionally triggers inflation and/or deflation, optionally periodic, of the intramembrane space as the two leaflets of the bilayer membrane that encloses the cell, the nucleus and other cell organelle such as the mitochondria, detaches and attaches periodically. The membrane of cells is then stretched, cell fibers and the cytoskeleton are loaded, and tension and compression of membrane proteins may be changed. In such a manner, cell(s) may be mechanically manipulated to change functioning. It should be noted that pressure amplitude may be applied with caution to avoid forming undesired ruptures on the membrane of the cell, see international patent applications numbers PCT/IL2011/000359 and PCT/IL2011/000360 which are incorporated herein by reference. The desired nondestructive mechanical force, for example the pressure amplitude, is selected so as to affect the functioning of the cells and the BLSs without or with little effect on the functioning of other cells which are exposed to ultrasound and/or light radiation with no microbubbles nearby. As used herein, a nondestructive mechanical force is a mechanical force which is applied on the membrane of cells without forming irreversible raptures.

Optionally, target information defining one or more characteristics of the cell(s), for example the membrane and/or additional information are received and used for calculating an energy transmission pattern to apply the desired nondestructive mechanical force by forming one or more pressure waves in proximity to cells. The instructions are then forwarded to the one or more energy sources which radiate accordingly the target area.

According to some embodiments of the present invention, there are provided methods and devices for stimulating the BLSs of target cells by producing localized and targeted pressure pulses using opto-acoustic heating of chromophore(s), such as gold nanoparticle(s) and/or oxy-hemoglobin in the red blood cells with and/or without ultrasound radiation. When the activation of the cells is based on light, the accuracy of targeting cells is reduced in about three orders of magnitude, from millimeter size (ultrasound) to micrometer size (light). The targeting of a target area may be performed by synchronizing light intensity and ultrasonic intensity. In such embodiments, each one of the transmission has less or no effect on areas around the target area. Optionally, BLS manipulation is made by radiating chromophores, with light (laser) and ultrasound radiation, while the laser is synchronized with the ultrasound to produce microbubbles around the chromophores.

According to some embodiments of the present invention, there are provided methods of applying a nondestructive mechanical force on a cell membrane of one or more cells in aqueous environment by inducing heat generated acoustic pressure wave(s) in proximity thereto. In use, an energy transmission pattern, which is set to apply a desired nondestructive mechanical force on a cell membrane of one or more cells in an aqueous environment, is provided. Then, a target area in proximity to the cells is radiated with synchronized ultrasound and focused light energy according to the energy transmission pattern. The synchronization allows reducing the focused light energy or the ultrasound energy which has to be radiated in proximity to the cells for applying the desired nondestructive mechanical force separately. In such a manner, the temperature of the cells is not substantially increased during the radiation thereof. Moreover, synchronization between the focused light energy and the ultrasound energy may extend the oscillation period and increase the expansion of the membrane in relation to the oscillation period and the expansion of the membrane when energy of only one of the energy types is applied.

According to some embodiments of the present invention, there are provided systems of applying a nondestructive mechanical force on a cell membrane of one or more cells in aqueous environment by inducing heat generated acoustic pressure waves in proximity to the cells. An exemplary system includes a computing unit which calculates an energy transmission pattern to apply a desired nondestructive mechanical force on a cell membrane of at least one cell in an aqueous environment and an interface which synchronizes the radiating of a target area in proximity to the cells with ultrasound energy and light energy according to the computed energy transmission pattern.

According to some embodiments of the present invention, there are provided methods and systems of applying a nondestructive mechanical force on a cell membrane of one or more cells by using a plurality of red blood cells as chromophores. In such embodiments, a plurality of red blood cells in an intrabody target area in proximity to target cell(s) are radiated according to an energy transmission pattern to induce a pressure pulse as an outcome of rapid thermal expansion therearound.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
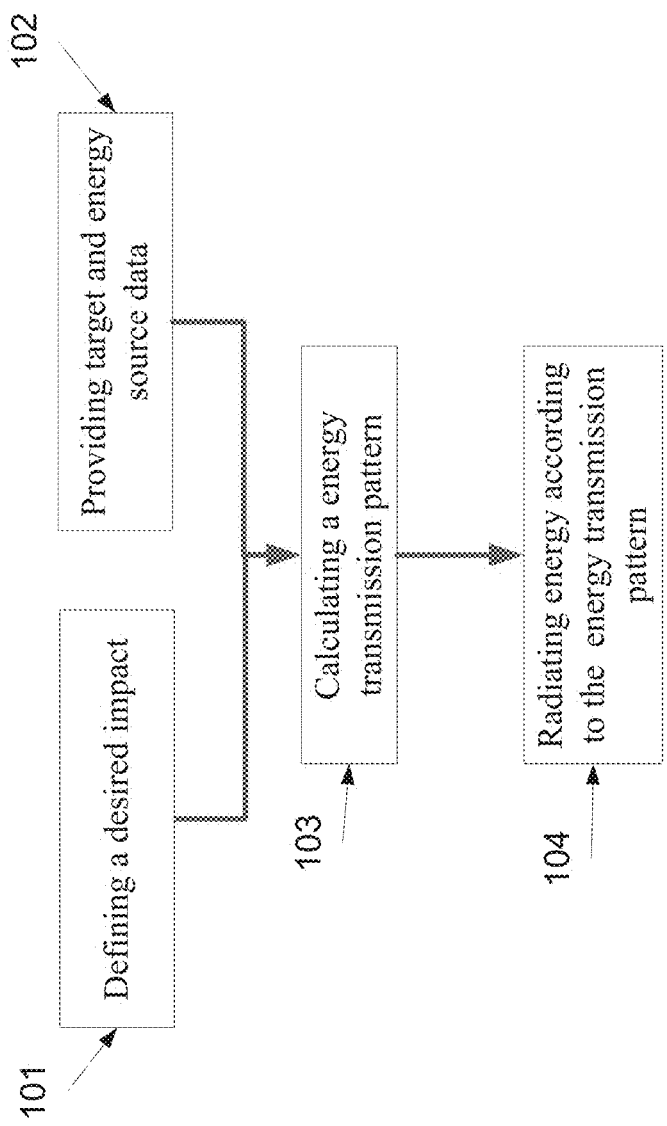

Reference is now made to FIG. 1A, which is a flowchart 100 of a method for calculating instructions for applying nondestructive mechanical force on target cell(s), for example cell membrane(s) of one or more target cells, in aqueous environment, for example an intrabody tissue by generating pressure pulses, optionally optoacoustic, in proximity thereto, for example by changing the temperatures of area(s) in the aqueous environment or forming vapor bubbles, optionally around chromophores, such as nanoparticles, according to some embodiments of the present invention. The resulting pressure pulses induce a revisable, nondestructive mechanical manipulation of the target cell(s). As used in this document, an heat generated acoustic pressure is a pressure which is applied by a thermal expansion and/or bubble(s) formed, optionally around chromophore(s) and induced, for example, by a combination of thermal expansion that follows light heating and applied ultrasound radiation and/or by a high repetition rate light pulses source, such as laser. As used in this document, a chromophore is a light absorbing element, such as nanoparticle(s).

In some embodiments, the pressure pulses, which are heat generated acoustic pressure pulses, are generated by simultaneously irradiating a target area with ultrasound energy, for example a focused beam of ultrasound, and light, for example a laser beam. Optionally, the transmissions of ultrasound energy and light are synchronized in order to reduce potential damage to the target tissue(s). As described in Boris Krasovitski et al., modeling photothermal and acoustical induced microbubble generation and growth, Ultrasonics, Vol. 47, No. 1-4. (December 2007), pp. 90-101. doi:10.1016, which is incorporated herein by reference, heating of chromophores, such as nanoparticles, by a laser pulse using energy density greater than 100 mJ/cm$^2$, could induce vaporization and generate microbubbles. The same result may be achieved by using ultrasound alone with acoustic pressure 4.5 MPa. When ultrasound is introduced at the same time as the laser pulse, less laser power is required and both acoustic pressure and laser energy are reduced to e.g. 5 mJ/cm$^2$ and 0.6 MPa correspondingly. Regarding the spatial resolution when US alone is acting a relatively high frequency is needed. For instance, a typical focus size of a focused beam of ultrasound at 1 MHz is about 1 millimeter. When using 50 MHz ultrasound the focal size is reduced to about 20 micrometers. And indeed 50 MHz might give the required resolution of tens of micrometers but the effectiveness of activation of the BLS as well as depth of penetration in the tissue are reduced dramatically with the frequency. It should be noted that it is complicated to aim radiation at a target of tens of micrometers and the inventors are not familiar with a simple and effective way to make ultrasonic energy absorbed in a selective way at a special location in the body. Microbubbles that do some acoustic energy absorption may be generated only by high intensity US or introduced into the blood as coated microbubbles for few minutes use only. All those problems are resolved when we use, as suggested here, a combined and synchronized action of unfocused US beam and localized heating of a chromophore, such as a nanoparticle, by a laser beam. A pulsating microbubble of few micrometer sizes, that is generated by boiling of the water around the heated nanoparticle, in a US field, can induce a combined pressure wave that will be localized around the nanoparticle. Since the pressure pulse propagates much further than the temperature rise we can find a distance tens micrometers away from the microbubble where the temperature rise will not harm the target cells and yet the combined pressure pulse will be strong enough to induce the required nondestructive stimulation. At the same time, all the cells, further away from will sense only the background pressure of the unfocused US field and this very low pressure will be below the threshold to induce any type of significant stimulation of the cells. To place the nanoparticle (or the nanoparticle cluster) in the exact location and to guarantee a safe distance from the of target cells one can use a separating gel coating, for example targeting the nanoparticles to the right group of cells can also be done by means of special ligand coating in vicinity to the microbubble.

The laser pulse should be given at about the time when the acoustic pressure is minimal, because the phase transition, i.e.

evaporation/boiling occurs then at the most favorable conditions and the energy needed to generate a bubble is minimal (for the given acoustic pressure pulse). As a result of the synchronization, this energy range is safe to be applied in-vivo and as such applicable for in vivo treatments. It should be noted that when vapor bubble(s) are forms, the amplitude of pressure pulse(s), such as heat generated acoustic pressure pulse(s), is substantially higher than the amplitude of similar pressure pulse(s) when no vapor bubble(s) are formed.

As further described below, according to some embodiments of the present invention, the nondestructive mechanical force is formed by changing the pressure that is applied on the cell membrane in the aqueous environment, for example by increasing vapor pressure around or near chromophores to boil locally the aqueous environment therearound and/or by heating areas in the aqueous environment using light pulses. As further described below, the process starts from heating of the chromophores with the energy delivered by one or more laser beams. In case vapor bubbles are formed, when the temperature of the chromophores reaches the boiling point of the surrounding liquid in the aqueous environment, vapor appears around the chromophores and when the irradiation ceases the vapor cools and collapses. The appearing and collapsing of the vapor bubbles is accompanied with heat and/or pressure impact on adjoining objects, see, for example V. P. Zharov et al. "Microbubbles-overlapping mode for laser killing of cancer cells with absorbing nanoparticle clusters" in J. Phys. D: Appl. Phys. 38 (2005) 2571-81, which is incorporated herein by reference.

Figure 1B:
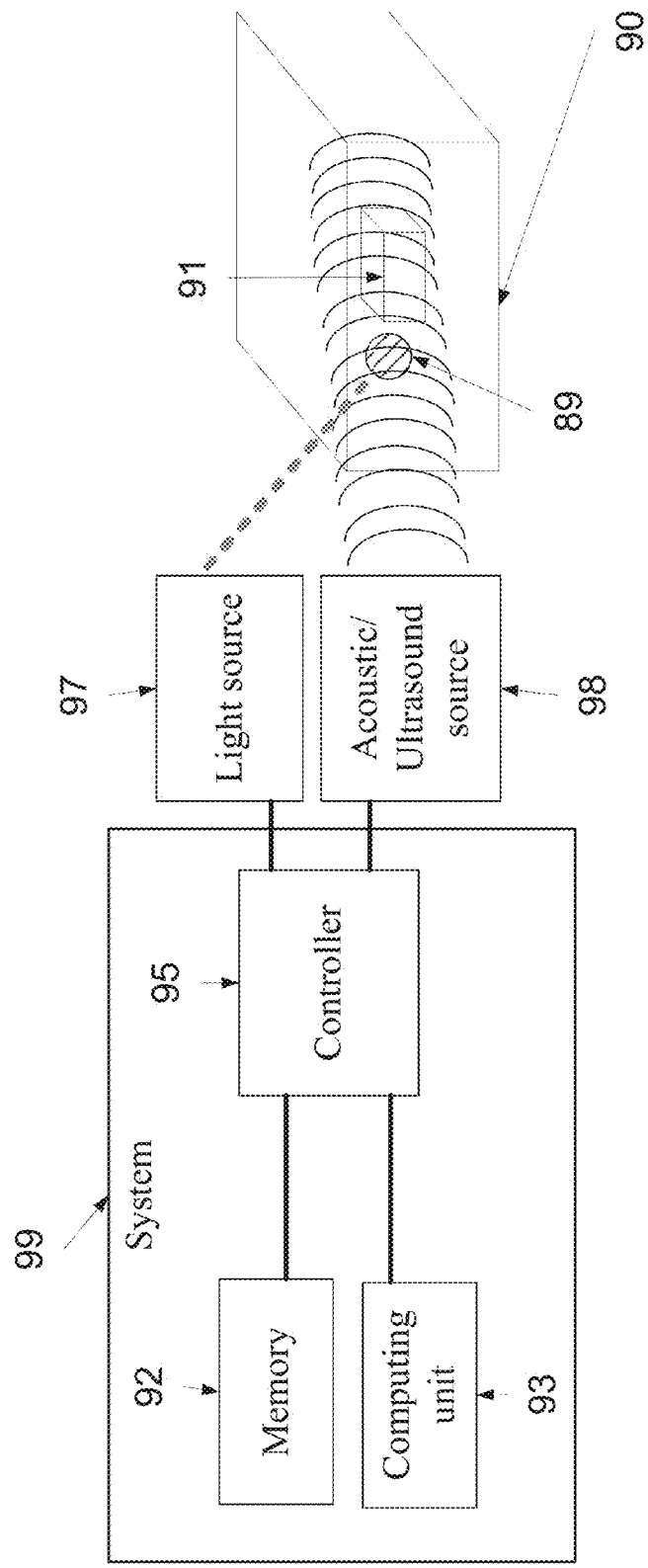

Reference is now also made to FIG. 1B, which is a schematic illustration of a system 99 of applying a nondestructive mechanical force on one or more cells 90 in aqueous environment by generating heat generated acoustic pressure pulses, according to some embodiments of the present invention. The system 99 is optionally used to implement the method depicted in FIG. 1B and/or used for applying precalculated and/or preset heat generated acoustic pressure pulses. Optionally, the system 99 is a neuro-stimulation device where the heat generated acoustic pressure pulses apply different mechanical forces on a neural tissue, for example as a neural interface. The system 99 is set to operate an acoustic wave source 98, such as a probe that includes a transducer or an array of ultrasound transducers each optionally separately controllable to be activated independently in a different fashion. The acoustic wave source may include an ultrasound source, such as a focused ultrasound (FUS) source, a high-Intensity focused ultrasound (HIFU) source and/or a magnetic resonance-guided focused Ultrasound (MRgFUS) source. This probe may be referred to herein as an ultrasonic source. In addition, the system 99 is set to operate a focused light source 97, such as a laser source.

The system 99 optionally includes a computing unit 93 which calculates an energy transmission pattern to generate optoacoustic pulse(s) in a target area where the optoacoustic pulse is calculated to apply a desired nondestructive mechanical force on one or more target cells, optionally of an intrabody tissue, in proximity to the target area. Additionally or alternatively instructions which follow such an energy transmission pattern are stored in a memory 92 of the system 99. The system 99 further includes an interface, such as a controller 95 that synchronizes the radiating of the target area in proximity to the target cells with synchronized ultrasound and light radiations according to said energy transmission pattern to form optoacoustic pulse(s) in the target area.

Optionally, the system 99 applies the energy which induces heat generated acoustic pressure in a target area 89 or a target space in proximity to one or more selected cells 91 which are optionally part of a tissue 90. The heat generated acoustic pressures may be selected according to a desired bioeffect, for example neural stimulation, and/or neural inhibition or a desired diagnosis. The cells may be in various tissues in a target organ or a part of a target organ, such as the brain, the eye and optionally the retina there therein, and/or any other neural system or network. The stimulation and/or inhibition may be used for restoring and/or creating a composite sensory perception for people who have a major deficiency in their sensory systems, such as blindness or deafness with varying degrees. Employing heat generated acoustic pressure to stimulate or otherwise modulate the activity in primary sensory cortices or in the retina and auditory cochlea if these are functioning, would allow a stream of sensory input from the outside world to the brain, considering spatial and/or temporal resolutions.

Reference is now made, once again, to FIG. 1A. First, as shown at 101, a desired impact on the target cell(s), for example the cell membranes of one or more cells, is provided. The desired impact is optionally adjusting the membrane surface tension of the cell(s) to a desired level, optionally for a desired period. For example, a desired impact is optionally applying a nondestructive mechanical force on the membrane surface of nerve and/or muscle cells and any other cells including endothelial cells, epithelial cells and bone cells (osteocytes) so as to change their membrane tension. The change opens and/or closes ion channels on the cell membrane, regulates the flow of ions across the membrane. Optionally, the desired impact is applying a nondestructive mechanical force that opens a gate that controls the ion flow via the ion channels. Also, pores might form in the membrane as a result of exposure to US and this can enhance membrane permeability and allows greater rates of transport of drugs. In the brain it has a special importance in opening the brain blood barrier. Any mechanical stimulation of the cell by the pulsating intra-membrane space can activate cascades of mechano-transduction processes in the cells which are in particular known as mechano-sensitive like Endothelial cells in the blood vessels, which are sensitive to shear stress, stretching force and pressure; Osteocytes in the bone and Chondrocytes in the particular cartilage which are sensitive to compression forces, and many others. Other examples for desired impacts are patterned auditory neuron stimulation for inner ear prosthesis, patterned retinal neuron stimulation for retinal prosthesis, patterned three dimensional stem cell differentiation on a tissue engineering scaffold for organ architecture, activation of implanted nerve prosthesis for nerve activation for muscle activation, activation of implanted pacemaker, and/or skin rejuvenation.

As shown at 102, information pertaining to the one or more of the following is provided: the target cell membrane(s), the target cell(s), and/or the surrounding environment wherein the heat generated acoustic pressure pulse(s) are generated for applying a mechanical pressure on the cell membrane(s). As further elaborated below, this information, referred to herein as target information, includes information about particles which around or near which the vapor bubbles may be formed, for example a potential of absorbing laser power by the chromophore, heating temperature(s), melted particle mass, chromophore total mass, and/or chromophore radius, information about the surrounding liquid, for example volume expansion coefficient(s) (also known as thermal expansion coefficient), density and/or dynamic viscosity of the liquid, initial temperature of vaporization, the latent heat of vaporization/condensation, and information about the power source that is used for generating the heat generated acoustic pressure pulse(s), for example the laser pulse width of a used laser sources, including scanners and holographic, and/or ultrasonic source. It should be noted that some of the parameters, for example the volume expansion coefficient(s), depends on the forming vapor bubbles or the avoidance from forming vapor bubble(s). This target information may be provided in advance, for example taken from a repository, such as a memory that hosts a plurality of different target information, each for another cell and/or for achieving a different impact on the target cells.

Now, as shown at 103, based on the target information provided above, an energy transmission pattern that is needed to achieve the desired impact is calculated and/or selected. Optionally, the calculation is based on the heat transfer and/or vaporization, the bubble and/or fluid dynamics, and/or dissolved gas transport. The calculation allows predicting the magnitude of the generated heat generated acoustic pressure pulse(s) and optionally the bubble stability when needed, and to define conditions for more effective heat generated acoustic pressure pulse(s) generation in terms of laser power and optionally ultrasound acoustic pressure.

The energy transmission pattern includes instructions to one or more power source(s) to radiate the environment around the cells, for example with chromophores as outlined above and further described below. The energy transmission pattern optionally defines the wavelength and/or the transmission period of the radiated energy.

Optionally, the energy transmission pattern is set so that temperature of the target cell(s) is not changed and/or not substantially changed. For example, reference is now made to FIG. 2, which is an isotherm of the temperature of a target area and isobars of a desired mechanical pressure generated by heat generated acoustic pressure as a function of the distance of a chromophore from the target area and a radiation period. The graph allows calculating an energy transmission pattern wherein the temperature of the target area does not substantially increase while the desired mechanical pressure is achieved. In this exemplary graph, the isobar is 1 bar gauge, the isotherm is 1° C. over the initial temperature, and granule diameter 2 μm, the pulse duration is 20 ns, laser beam intensity 2.4 MW/cm$^2$, and an absorption efficiency.

Reference is now made, once again, to FIG. 1A.

Now, as shown at 104, instructions to one or more energy source are set according to the calculated energy pattern. These instructions instruct a light source, such as a laser source, and optionally an ultrasound source to radiate a target area in proximity to the target tissue(s) according to the energy transmission pattern. The radiation is optionally performed on one or more chromophores, which are placed in a common aqueous environment with the target tissue(s). Optionally, the chromophores are intrinsic to the tissue of the target cell(s). For example, flavoproteins may be used as chromophores to form heat generated acoustic pressure in proximity to cells of certain tissues. Additionally or alternatively, the chromophores may be melanin or Retinal pigment epithelium (RPE).

The above method allows forming pressure pulses, optionally optoacoustic, that apply a desired mechanical pressure on target cells. The desired mechanical pressure is set for a desired reversible manipulation, such as a membrane manipulation, for example an inflation and/or deflation, optionally periodic, of the intramembrane space as the two leaflets of the bilayer membrane that encloses the cell. The membrane is then stretched, cell fibers and the cytoskeleton are loaded, and tension and compression of membrane proteins is changed. In such a manner, cell(s) may be mechanically manipulated to change functioning. This may be used for stimulating nerve cells and adjusting tissue permeability, for example for changing drug delivery rates. The stimulation may be applied on blood-brain barrier (BBB) cells for effecting its operation and/or on broken bones and/or wounds to urge their healing rate and/or the like.

For example, high spatial resolution (micrometer-scale) as well as high temporal resolution (sub-millisecond) of the pressure pulses allows manipulating groups of nerve cells that carry the signals to the brain from the retina in retinal implants and from the ear in cochlear implants. Today, ear implants are quite limited in their performance while retinal implants are still being developed. Various types of nondestructive stimulation of cells by US may be an outcome of the effect of the pressure pulse on the BLSs in and around the cell. Same effects can be produced by pressure pulse that were not produced by US only but that were generated by the combined action of a microbubble created around or near a laser heated nanoparticle e.g. and US or by the combined action of an expansion wave created by a laser heating of a chromophore (without a microbbuble) and US. The only difference is in terms of spatial resolution "US only" cell stimulation has poor spatial resolution of about one millimeter so that it is not accurate enough for manipulation of individual cells or even small groups of cells, e.g. in the nervous system. Also, RF heating or other types of electromagnetic stimulation that is not based on arrays of microelectrodes has both poor spatial and temporal resolution, and it is a major technical challenge to bring an array of microelectrodes close enough to the target cells. Here we propose a method for a combined action of laser induced chromophore heating that produces a heat generated acoustic pressure pulse (through a pulsating bubble around a heated nanoparticle or by a thermal expansion of the tissue) that is synchronized with the US pressure pulse and both act together on the cells in the target zone like US does, to stimulate them nondestructively is a safe method for cell modulation of functioning with a very high spatial resolution. This optoacoustic radiation sources may be placed more than few millimeters from the target area, for example several centimeters away and has no influence on the tissue(s) surrounding the target area.

Moreover, when the ultrasonic radiation oscillates the membrane of the target cell(s), the effect of the optoacoustic pulse may be intensified. In such embodiment, the formation of the pulse is optionally coordinated with the oscillation of the membrane to increase the effect of the optoacoustic pulse and/or to allow applying less mechanical force on the cell(s).

Finally, the combined action of the light-induced heating and ultrasound induced mechanical effect can also be synergistic at the biological level. For example, heating can lead to superthreshold response (e.g. intracellular calcium release or membrane potential change) in a subset of cells, which the mechanical effect compounds to a superthreshold event.

Figure 1C:
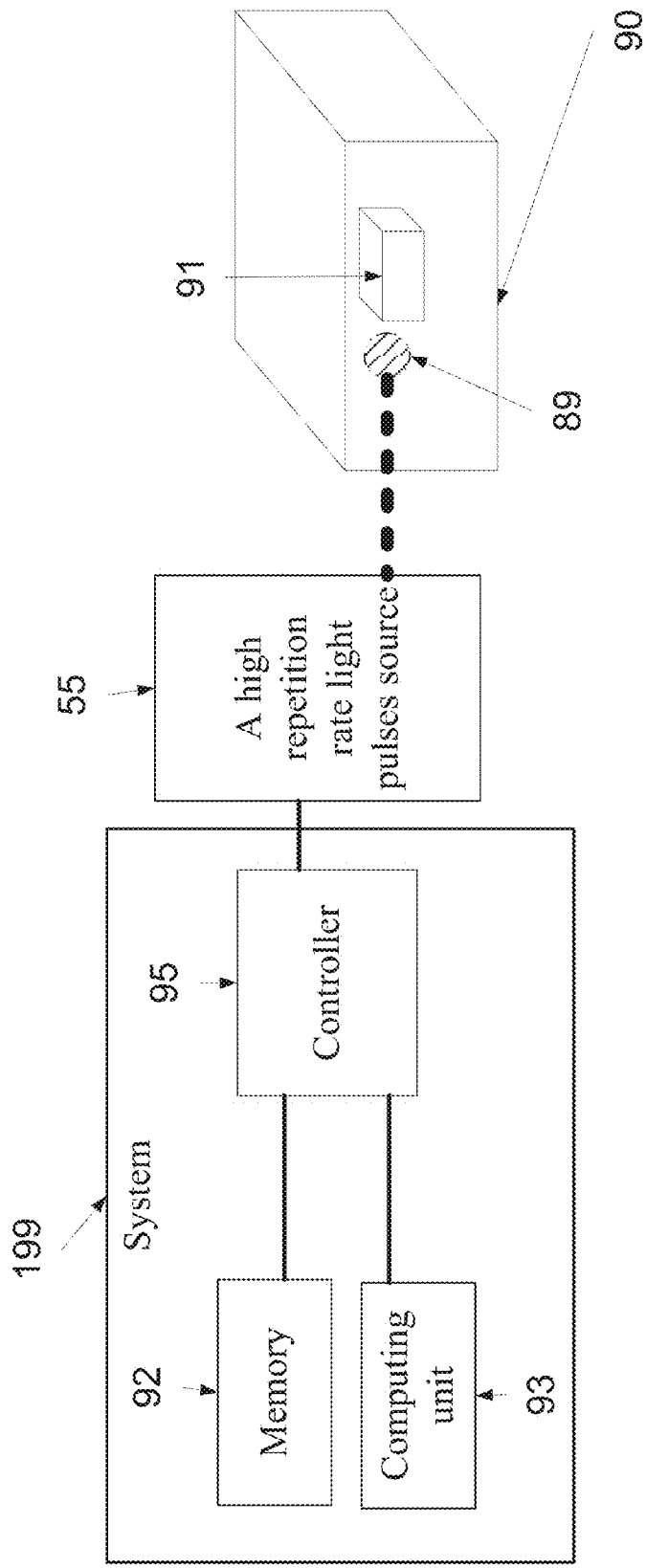

According to some embodiments of the present invention, the heat generated acoustic pressure pulses are induced using a heat generated acoustic pressure source, such as a laser, and optionally without any independent acoustic energy source. In such embodiments, there may be no need to synchronize sources of different radiations. For example, reference is now also made to FIG. 1C, which is a schematic illustration of a system 199 that uses a high repetition rate light pulses source 55 for applying a nondestructive mechanical force by inducing heat generated acoustic pressure pulses, according to some embodiments of the present invention. Some of the components of the system 199 are as depicted in FIG. 1B (89-93 and 95); however, FIG. 1C further depicts the high repetition rate light pulses source 55, for example a laser source, that is controlled by the controller 95 instead of the light source 97 and the acoustic/ultrasonic source 98. In use, the high repetition rate light pulses source 55 is instructed by the controller 95 to generate pulses or is modulated at a rate of 100 kHz or more, causing a periodic cavitation around each chromophore to stimulate the cells. In use, the high repetition rate light pulses source 55 transmits a pulsating and/or a temporally-modulated light beam or light pattern toward at the target area 89. The modulation rate of the transmission is higher than a natural cavitation frequency of the chromophore, for example the rate is higher than 100 kHz and slower than 1 MHz, for example about 30 MHz, 50 MHz, 65 MHz, and 80 MHz.

Figure 1D:
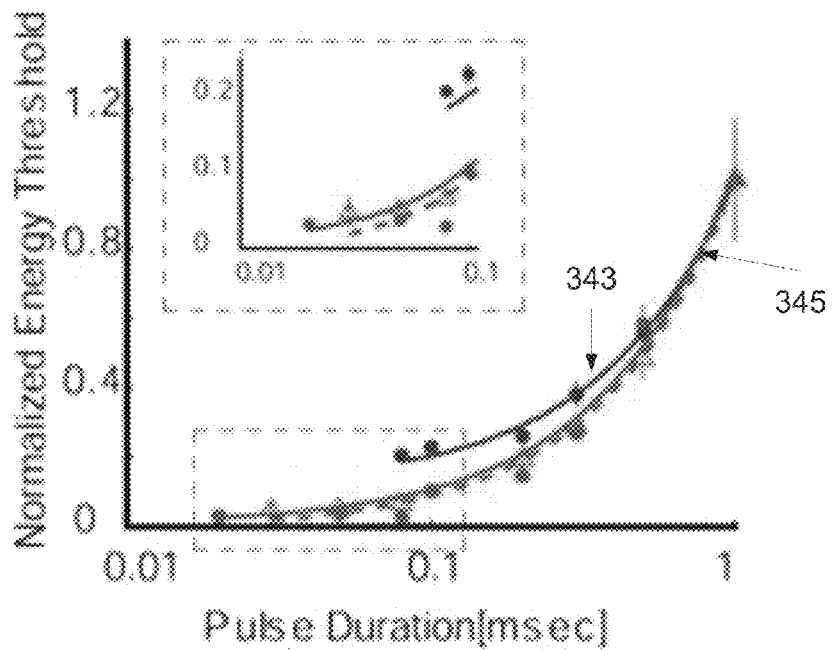
Figure 1E:
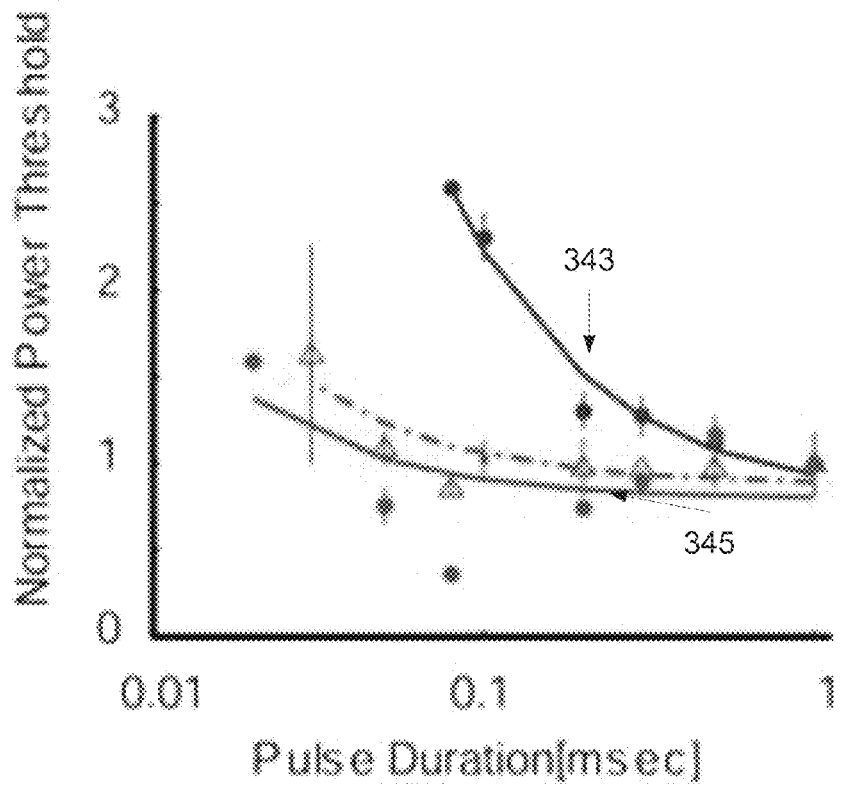

Similarly to the described above, the system 199 may be used to stimulate or otherwise modulate the activity of a cell, such as a nerve, for example in primary sensory cortices or in the retina and auditory cochlea. For example, reference is now made to FIGS. 1D and 1E, which are graphs depicting activation thresholds (normalized energy and power) for exciting cortical neurons by directing light onto chromophores, such as black microparticles, Line 343 is related to a continuous laser and line 345 is related to a repetition rate light pulses source, a rapidly pulsed laser with a pulse rate of pulse per 12.5 nanoseconds (80 MHz). As depicted in the graph, the rapidly pulsed laser has excitation thresholds which are more effective in driving neural activity when excitation is performed at low durations (e.g. less than 200 microseconds). When an acoustic wave with a frequency of 500 kHz (+−200 kHz) is generated by the chromophores in response to a pulsating laser (not during a CW pulse) coactivation of acoustic and photo-thermal energy generated at the chromophores is responsible for lower activation thresholds.

Reference is now made to a set of equations that allows calculating such energy transmission pattern.

As described hereinbelow, some of the equations include mathematical description of a vaporization process for forming for a vapor bubble in proximity to the target cells, for example around or near one of the plurality of nanoparticles. The mathematical description is for developing a vapor bubble around a single chromophore, however can be used for developing vapor bubbles around a plurality of chromophores.

As described hereinbelow, some of the equations include mathematical description of generating mechanical pressure on target cells by heat generated acoustic pressure pulses which heat one or more areas in proximity thereto, for example around one of the plurality of chromophores.

When, assuming spherical symmetry, the heat transfer equation for the liquid surrounding a nanoparticle with radius $R_p$ is:

Equation 1

$$\frac{\partial T_L}{\partial t} = \frac{D_L}{r^2} \frac{\partial}{\partial r}\left(r^2 \frac{\partial T_L}{\partial r}\right);$$
$$0 < t < t_0;$$
$$R_p \leq r < \infty.$$

where $T_L$ denotes surrounding liquid temperature, t and r denote time and space coordinates, $D_L$ denotes heat diffusivity of the surrounding liquid and $t_0$ denotes a moment when the evaporation begins. The boundary conditions are of temperature continuity on the particle surface:

Equation 2:

$$T_L|_{r=R_p} = T_p(t). \tag{2}$$

where $T_p$ denotes the temperature of the particle when the temperature away from the cell membrane is:

Equation 3:

$$T_L|_{r=\infty} = T_\infty. \tag{3}$$

The initial condition is:
Equation 4:

$$T_L|_{t=0} = T_\infty. \tag{4}$$

A lumped heat balance equation for the particle is:

Equation 5

$$\frac{4}{3}\pi R_p^3 c_p \rho_p \frac{dT_p}{dt} = q + 4\pi R_p^2 k_L \frac{\partial T_L}{\partial r}\bigg|_{r=R_p}$$

where the lumped heat balance consists the accumulation of the heat term on the left hand side (LHS) of Equation 5 and the source term q and heat loss by conduction to the surrounding liquid on the right hand side (RHS) of Equation 5. The source term is expressed as follows:

$$q_L \text{ for } 0 < t < t_w;$$

$$q = 0 \text{ for } t > t_w;$$

where $q_L$ denotes a laser power absorbed by the particle and $t_w$ denotes the laser pulse width. The initial condition is:
Equation 6:

$$T_p|_{t=0} = T_\infty.$$

The evaporation begins when $T_p = T_{s0}$, where $T_{s0} = T_s(p_{s0})$ denotes the initial temperature of vaporization, and $p_{s0}$ is the corresponding vapor pressure:

Equation 7

$$p_{s0} = P_{amb} + \frac{2\sigma(T_{s0})}{R_p}.$$

where $P_{amb}$ (t) denotes an ambient pressure and σ denotes a surface tension.

Now, after the particle temperature reaches the liquid vaporization temperature $T_{s0}$, a spherical layer of vapor starts to form around or near the particle with an inside radius $R_p$ and outside moving boundary with a radius R that varies in time. A heat transfer problem becomes a two-phase problem with a vapor layer having a thickness of $R-R_p$ and a liquid surrounding the vapor layer. Also, the moving boundary acts like a moving spherical piston pushing liquid outward symmetrically when the vapor layer expands. Mass conservation of incompressible fluid (continuity) dictates that the outward flow velocity at radius r is proportional to $r^{-2}$. The heat transfer equation for the surrounding liquid is, therefore:

Equation 8

$$\frac{\partial T_L}{\partial t} + \frac{R^2}{r^2}\frac{dR}{dt}\frac{\partial T_L}{\partial r} = \frac{D_L}{r^2}\frac{\partial}{\partial r}\left(r^2 \frac{\partial T_L}{\partial r}\right);$$
$$t > t_0;$$
$$R \leq r < \infty,$$

where the second term on the LHS is a term of advection added in flowing liquid, see Hao Y, and Prosperetti A The dynamics of vapor bubbles in acoustic pressure fields. *Phys-*

*ics of Fluids*, 1999; 11(8): 2008-2019, which is incorporated to herein by reference. The liquid temperature at the vaporization boundary r=R is:

Equation 9:

$$T_L|_{r=R} = T_s(p_s).$$

where

Equation 10

$$p_s = p_{amb} + \frac{2\sigma(T_s)}{R}.$$

The radius of the vapor bubble changes as a result of vaporization/condensation on its boundary $$\left(\frac{\partial R}{\partial t}\right)_{vc}$$

and expansion/collapse due to the pressure difference across the water/vapor boundary Equation 11

$$\left(\frac{\partial R}{\partial t}\right)_d:$$

$$\frac{dR}{dt} = \left(\frac{\partial R}{\partial t}\right)_{vc} + \left(\frac{\partial R}{\partial t}\right)_d$$

The heat balance at the vaporization/condensation boundary is:

Equation 12

$$\rho_L L \left(\frac{\partial R}{\partial t}\right)_{vc} = q_H + \lambda_L \frac{\partial T_L}{\partial r}\bigg|_{r=R+0};$$

and the initial condition is:
Equation 13:

$$R_{t=t^*} = R_p;$$

where t* denotes the time when the vapor bubble appears, L denotes the latent heat of vaporization/condensation, and $q_H$ denotes the heat flux from the vapor to the vaporization/condensation boundary.

The heat flux from the particle to the vapor layer ($q_H$) can be expressed by:

Equation 14

$$q_H = k_g \frac{R_p}{R} \frac{(T_p - T_s)}{(R - R_p)}$$

assuming that the surrounding gas layer is thin and the heat is transferred only by conduction. Here $T_s$ is the vaporization temperature, and $k_g$ is the heat conductivity of the vapor/air mix. For larger shell thicknesses, heat convection should be taken into account and the heat flux may be expressed as following:

Equation 15:

$$q_H = \alpha(T_p - T_s)$$

where α denotes convective heat transfer coefficient for the case when there is a space between two spherical surfaces, see H. Y. Wong, Handbook of essential formulae and data on heat transfer for engineers, Longman, London and New York. 1977, which is incorporated herein by reference.

As described above, the evaporation is performed according to a heat balance equation calculated per particle. The heat balance equation may be adapted to the melting temperature of the used nanoparticle.

Optionally, if the particle temperature is lower than the melting temperature $T_p < T_m$, the heat balance equation is as follows:

Equation 16

$$\frac{4}{3}\pi R_p^3 c_p \rho_p \frac{dT_p}{dt} = q - 4\pi R_p^2 q_H. \tag{16}$$

Alternatively, if the particle temperature reaches the melting temperature $T_{pm}$ at the time moment $t = t_{ms}$ the melting process begins, while the particle temperature stays constant. Introducing a new variable, melted part variable, which is defined as follows:

Equation 17

$$r_m = \frac{m_m}{m_p}, \tag{17}$$

Where $m_m$ denotes a melted mass of the nanoparticle and $$m_p = \frac{4}{3}\pi R_p^3 \rho_p$$

denotes the particle total mass. In such embodiments, the following heat balance to equation may be used:

$$\frac{4}{3}\pi R_p^3 \rho_p L_{pm} \frac{dr_m}{dt} = q_m - 4\pi R_p^2 q_H \qquad \text{Equation 18}$$

with initial condition:
Equation 19:

$$r_m|_{t=t_{ms}} = 0$$

where $L_{pm}$ denotes a melting latent heat of the particle material and $q_m$ denotes power absorbed by the melted particle from laser. The melting process ends at the time moment $t_{me}$ when $r_m = 1$. During time interval $t_{ms} < t < t_{me}$, $T_p = T_{pm}$ is assumed.

Optionally, if the particle temperature reaches the vaporization temperature $T_{pv}$ at the time moment $t = t_{vs}$ the vaporization process begins, while the particle temperature preserves the constant value $T_{pv}$. Introducing a new variable, vaporized part variable, which is defined as follows:

$$r_v = \frac{m_v}{m_p},$$ Equation 20 where $m_v$ denotes the vaporized mass of the particle. In such embodiments, the following heat balance equation may be used:

$$\frac{4}{3}\pi R_{pm}^3 \rho_p L_{pv} \frac{dr_v}{dt} = q_v - 4\pi R_{pm}^2 q_H$$ Equation 21 with initial condition:
Equation 22:

$$r_v|_{t=t_{vs}} = 0.$$

where $L_{pv}$ denotes vaporizing latent heat of the particle material, $R_{pm}$ denotes a to radius of non vaporized part of the particle, and $q_v$ denotes power absorbed by this part. In this calculation, the energy absorption of the vaporized particle neglected and the time interval is assumed $T_p = T_{pv}$.

Evolution of the Vapor Bubble

Changes in the radius of the nanobubble that is developed around a particle are determined by pressure differences as described by the Rayleigh-Plesset equation, see A. Prosperetti and A. Lezzi: "Bubble dynamics in a compressible liquid Part 1. First order theory." in J. Fluid Mech. 168, 457-478 (1986), which is incorporated herein, for example as follows:

$$R\left(1 - \frac{u}{C}\right)\frac{du}{dt} + \frac{3}{2}u^2\left(1 - \frac{u}{3C}\right) =$$ Equation 23
$$\frac{1}{\rho_L}\left[\left(1 + \frac{u}{C}\right)\left(p_g - P_0 - \frac{2\sigma}{R} - \frac{4\eta_L}{R}u\right) + \right.$$
$$\left.\frac{R}{C}\left(\frac{dp_g}{dt} + \frac{2\sigma}{R^2}u + \frac{4\eta_L}{R^2}u^2 - \frac{4\eta_L}{R}\frac{du}{dt}\right)\right].$$

where $u \equiv \left(\frac{\partial R}{\partial t}\right)_d$ and $\rho_L$ and $\eta_L$ denote respectively density and dynamic viscosity of the liquid, and C denotes sound velocity in the gas. Optionally, when light pulses are applied simultaneously with ultrasound radiation and the ambient pressure is expressed as follows:
Equation 24:

$$R = R_p; u = 0.$$

The pressure inside the shell of the bubble, denoted herein as $p_g$, is calculated by summing partial pressures of the vapor and the air diffusing from the surrounding liquid:
Equation 25:

$$p_g = p_v + p_a + p_p;$$

where $p_v$ denotes the vapor partial pressure inside the bubble and $p_a$ denotes the air partial pressure inside the bubble. The partial pressures of the vapor, air and vaporized particle may be expressed as:

$$p_a = \frac{3n_a R_g T_v}{4\pi(R^3 - R_p^3)};$$ Equation 26

$$p_v = \frac{3n_v R_g T_v}{4\pi(R^3 - R_p^3)};$$

-continued $$p_p = \frac{R_g T_{pv} \rho_p R_p^3 (1 - r_v)}{\mu_p [R^3 - (1 - r_v)R_p^3]}.$$

where $n_v$ and $n_a$ denote the mole contents of the vapor and air correspondingly. The vapor mole content inside the bubble is connected with thickness of the vaporized liquid:

$$\frac{dn_v}{dt} = 4\pi R^2 \frac{\rho_L}{\mu_v}\left(\frac{\partial R}{\partial t}\right)_{vc}$$ Equation 27 where $\mu_v$ denotes vapor molecular weight.

Air Diffusion into the Bubble

The mole content of the air inside the bubble is determined by the mass balance:

$$\frac{dn_a}{dt} = -\frac{\rho_a G_a}{\mu_a} = 4\pi R^2 D_a \frac{\partial C_a}{\partial r}\bigg|_{r=R}$$ Equation 28 where $G_a$ denotes a volume rate of the air leaving the bubble, $\mu_a$ and $\rho_a$ denote air molecular weight and density respectively, $D_a$ denotes the diffusivity of the air in the surrounding liquid, and $C_a$ denotes mole concentration of the air in the surrounding to liquid.

The diffusion of air in the liquid may be described using the Fourier equation:

$$\frac{\partial C_a}{\partial t} + \frac{R^2}{r^2}\frac{dR}{dt}\frac{\partial C_a}{\partial r} = \frac{D_a}{r^2}\frac{\partial}{\partial r}\left(r^2 \frac{\partial C_a}{\partial r}\right);$$ Equation 29

$t > t_0;$ $R < r < \infty.$ with the following initial and boundary conditions:
Equation 30:

$$C_a(r,0) = C_i; r > R_p; \text{ and}$$

Equation 31:

$$C_a|_{r=R} = C_s; t > 0.$$

where $C_s$ denotes air concentration on the bubble surface. It is assumed that $C_s$ equals the saturation concentration, see A. Eller and H. G. Flynn, "Rectified diffusion during nonlinear pulsations of cavitation bubbles" in J. AcoustSoc Am. 37, 493-503 (1965), which is incorporated herein by reference. The saturation concentration is related to the air partial pressure by Henry's law:

$$C_s = \frac{p_a}{k_a}$$ Equation 32 where, $k_a$ denotes the Henry's constant.

Shock Waves

The collapse of a vapor bubble may be accompanied by high gas pressure inside the vapor bubble, which in turn causes spreading of shock waves in vicinity of the vapor bubble. Parameters of the shock waves may be estimated based on the Kirkwood-Bethe approximation (see R. T. Knapp, J. W. Daily and F. Hammit: "Cavitation". McGraw- Hill New York, 1970), which are incorporated herein by reference. The equations of continuity and motion for surrounding liquid are:

$$\frac{\partial \rho_L}{\partial t} + \frac{2\rho_L}{r}v + \rho_L \frac{\partial u}{\partial r} + u\frac{\partial \rho_L}{\partial r} = 0;$$

and $$\rho_L \frac{\partial v}{\partial t} + \rho_L v \frac{\partial v}{\partial r} + \frac{\partial P}{\partial r} = 0;$$

Based on the technique the following function is introduced:

Equation 33:

$$y = r(h + v^2/2)$$

where h denotes enthalpy difference between liquid of pressures p and $P_0$ $$h = \int_{P_0}^{p} \frac{dp}{\rho}. \qquad \text{Equation 34}$$

Parameter y preserves its value along characteristic traced by a point moving with velocity C+v. C($\rho$) denotes a local sound velocity:

$$C = \sqrt{\frac{\partial P}{\partial \rho_L}}. \qquad \text{Equation 35}$$

The latter function may be determined from the surrounding liquid equation of state. For water the equation may be written as following (Tait equation):

$$\frac{p + B}{P_0 + B} = \left(\frac{\rho_L}{\rho_{L0}}\right)^n. \qquad \text{Equation 36}$$

where [P]=Pa, [$\rho$]=kg/m³, B=314 MPa, n=7. The hypothesis leads to equations:

$$\dot{v} = \frac{1}{C - v}\left[(C + v)\frac{y}{r^2} - \frac{2C^2 v}{r}\right]; \qquad \text{Equation 37}$$

where $\dot{r} = v + C$.
The pressure p at r=r(t) may be calculated as follows:

$$p = (P_0 + B)\left[\left(\frac{y}{r} - \frac{v^2}{2}\right)\frac{(n-1)\rho_{L0}}{n(P_0 + B)} + 1\right]^{\frac{n}{n-1}} - B. \qquad \text{Equation 38}$$

Based on this expression the value of the shock wave pressure on the membrane situated on distance d from the particle center equals to:

$$P_f = p(t, d) = (P_0 + B)\left[\left(\frac{y}{d} - \frac{v^2}{2}\right)\frac{(n-1)\rho_{L0}}{n(P_0 + B)} + 1\right]^{\frac{n}{n-1}} - B. \qquad \text{Equation 39}$$

Impact on the Cell Membrane

In order to estimate the mechanical impact of the shock waves on the cell membrane the technique developed earlier, see B. Krasovitski et al. "Intramembrane cavitation as a unifying mechanism for ultrasound-induced bioeffects" in PNAS (2011), which his incorporated herein by reference, may be used. Consider a bilayer membrane of diameter 2a and a nanoparticle placed near the membrane at distance d. The system sonicates the nanoparticle(s) using ultrasound energy in a synchronized manner with irradiating the nanoparticle(s) with a relatively short laser pulse. As a result, the nanoparticle(s) is heated and a vapor bubble appears therearound. When the laser pulse ends the particle cools and the bubble collapses. The rise and collapse of the bubble is accompanied with spreading of shock waves which may reach the membrane as a pressure $P_f$ and together with the ultrasound pressure $P_A$ induces its to deformation, namely the deviation of one leaflet from its equilibrium position. This intra membrane inflation is measured at any moment by the height of the dome at its apex (H) and is described by following equations, see also B. Krasovitski et al. "Intra membrane cavitation as a unifying mechanism for ultrasound-induced bioeffects" in PNAS (2011):

For H>$H_{min}$:

$$\frac{d^2 H}{dt^2} + \frac{3}{2R}\left(\frac{dH}{dt}\right)^2 = \qquad \text{Equation 40}$$

$$\frac{1}{\rho_l R}\left[P_{in} + P_{ar} - P_0 + P_A \sin\omega t - P_{st}(R) - P_s(R) - P_f - \frac{4}{R}\frac{dH}{dt}\left(\frac{3\delta_0 \mu_s}{R} + \mu_l\right)\right].$$

For H<$-H_{min}$:

$$\frac{d^2 |H|}{dt^2} + \frac{3}{2R}\left(\frac{dH}{dt}\right)^2 = \qquad \text{Equation 41}$$

$$\frac{1}{\rho_l R}\left[-P_{in} - P_{ar} + P_0 - P_A \sin\omega t - P_{st}(R) - P_s(R) - P_f - \frac{4}{R}\frac{d|H|}{dt}\left(\frac{3\delta_0 \mu_s}{R} + \mu_l\right)\right].$$

where $\rho l$ denotes a density of surrounding liquid, $\mu_l$ denotes a dynamic viscosity of the liquid, $\mu_s$ denotes a dynamic viscosity of the membrane, $\delta_0$—denotes initial thickness of the membrane, $P_{st}$ denotes pressure attributed to surface tension, and R denotes the membrane curvature radius, connected with the membrane deviation H, and the membrane radius a as:

$$R = \frac{a^2 + H^2}{2H}; \qquad \text{Equation 42}$$

where $P_{st}$, the pressure attributed to surface tension, is calculated as follows:

$$P_{st}(R) = \frac{2(\gamma_1 + \gamma_2)}{R}, \qquad \text{Equation 43}$$

where $\gamma_1$ and $\gamma_2$ denote surface tension at the air-membrane and liquid-membrane interfaces respectively, $P_{sh}$ denotes a shock wave pressure caused by evolution of the vapor bubble, $P_{ar}$ denotes a pressure caused by attraction/repulsion forces, $P_{in}$ denotes the internal gas pressure, $\mu_s$ denotes dynamic viscosity of the to membrane and $\delta_0$ denotes initial thickness of the membrane.

Optoacoustic Generation of a Pressure Pulse by Laser Heating of a Chromophore

Reference is now made to a description of a model for the generation of a pressure pulse using a focused light source (laser) that heats a natural chromophore, for example a cluster of hemoglobin molecules in the RBC, pigmented granules in the eye retina, and/or heat sensitive liposomes. It should be noted that the natural chromophore light absorption efficiency, is much higher than the surrounding tissue. For example, in the pigmented epithelium layer up to 90% of the radiation energy is absorbed by melanoprotein granules of spherical and spheroidal shape and sizes of about 0.5-1 µm. In addition, it should be noted that the light intensity is low enough such that no boiling is induced and no vapor bubble is generated. Only a pressure pulse that accompanies the rapid thermal expansion and contraction is applied.

Heating of the Chromophore (Spherical Particle)/lliquid System a. Heat Transfer Problem When the spherical particle is of diameter 2a and subjected to laser irradiation of intensity I, the power absorbed by the particle may be expressed as:

Equation 43:

$$Q = K_{ab} S_p I.$$

where $K_{ab}$ denotes the absorption efficiency and $S_p$ denotes geometrical cross section of the particle.

In this embodiment, the heat transfer equation for the particle—surrounding tissue system is:

$$\frac{\partial T}{\partial t} = \frac{D(r)}{r^2} \frac{\partial}{\partial r}\left(r^2 \frac{\partial T}{\partial r}\right) + \frac{q(r)}{\rho(r)c(r)};$$

$$0 \leq r < \infty.$$

Equation 43 where q, W/m³ denotes a specific laser power absorbed.

Assuming that energy absorption of the particle much higher than one of surrounding tissue the following expressions may be set:

$q_0$; $0 < r < a$; $0 < t < t_p$;
$q = 0$; a 21 $r < \infty$; $0 < t < \infty$
0; $0 < r < \infty$; $t_p < t < \infty$ where $q_0$ is a specific laser power absorbed by the particle.

$$q_0 = \frac{3}{4} \frac{Q}{\pi a^3}.$$

Equation 45 c equals $c_b$ at $0 < r < a$ and $c_L$ at $r > a$, D equals $D_b$ at $0 < r < a$ and $D_L$ at $r > a$ and c equals $c_b$ at $0 < r < a$ and $c_L$ at $r > a$.

Boundary Conditions:

$$T|_{r=\infty} = T_0; \left.\frac{\partial T}{\partial r}\right|_{r=0} = 0.$$

Equation 46

Initial Condition:
Equation 47:

$$T|_{t=0} = T_0.$$

Dynamics Equation for Optoacoustic Heating

The dynamic equation of optoacoustic may be written in the following form, see Chia-Lun Hu. Spherical model of an acoustical wave generated by rapid laser heating in a liquid. JASA, v. 46, N3, Part 2, 1969, which are incorporated herein by reference:

$$\frac{\rho}{B} \frac{\partial^2 \phi}{\partial t^2} = \frac{1}{r^2} \frac{\partial}{\partial r}\left(r^2 \frac{\partial \phi}{\partial r}\right) - \beta(T - T_0)$$

Equation 48

Where B equals $B_b$ at $0 < r < a$ and $B_L$ at $r > a$; $\beta$ equals $\beta_b$ at $0 < r < a$ and $\beta_L$ to at $r > a$.

$\phi$ denotes a potential of displacements where $$u_r \equiv \frac{\partial \phi}{\partial r},$$

B denotes bulk modulus and $\beta$ denotes a volume thermal expansion coefficient.

Excessive pressure in the spherical symmetry case may be found as following:

$$p = -B\nabla \cdot \vec{u}$$

$$= -B\left(\frac{\partial u_r}{\partial r} + \frac{2u_r}{r} - \beta(T - T_0)\right)$$

$$= -B\left(\frac{\partial^2 \phi}{\partial r^2} + \frac{2}{r}\frac{\partial \phi}{\partial r} - \beta(T - T_0)\right)$$

Equation 49 where the first boundary condition:

$$\left.\frac{\partial \phi}{\partial r}\right|_{r=0} = 0.$$

Equation 50 the second boundary condition is:

$$\left.\frac{\partial \phi}{\partial r}\right|_{r=\infty} = 0.$$

Equation 51 and initial conditions are:

$$\phi|_{t=0} = 0; \left.\frac{\partial \phi}{\partial t}\right|_{t=0} = 0.$$

Equation 52

It is expected that during the life of a patent maturing from this application many relevant systems and methods will be developed and the scope of the term computing unit, a controller, a light source, and an ultrasound source is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and to "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions; illustrate some embodiments of the invention in a non limiting fashion.

To illustrate the effectiveness in deforming the BLS by the combined application of ultrasound and synchronized laser pulse, several cases were tested in which the maximal deviation of one leaflet from the other ($H_{max}$) is calculated. In the first case, shown in FIG. 3 the membrane diameter is 50 nm, nanoparticle diameter is 40 nm, and the distance between the particle center and the membrane 1,000 nm (distance between the particle center and the membrane) no ultrasound was applied, only laser pulse. The figure depicts oscillation of the membrane in response to shock wave induced by the growing and collapsing of a vapor bubble around the nanoparticle which is subjected to laser pulse.

Two shock waves, 1 micrometer away from the nanoparticle, are shown in FIG. 4, at the BLS, by the colored pink line which is marked with the title "shock wave pressure". In FIG. 4, the membrane diameter is 50 nm, the nanoparticle diameter is 40 nm, the distance between the particle center and the membrane is 1,000 nm, the ultrasound acoustic pressure is 1.6 bar, and the ultrasound frequency is 10 MHz.

The shock wave is attributed to a sudden expansion of the microbubble that accompanies the beginning of the boiling/evaporation stage, and the second that results from the sudden collapse of the microbubble as it cools down. The deformation of the membrane that is induced by the two shock waves is depicted in FIG. 5 that depicts the oscillation of membrane affected by ultrasound where the membrane diameter is 50 nm, the acoustic pressure is 1.6 bar and the ultrasound frequency is 10 MHz. The deformation is typified by a relatively long and large expansion followed by a train of smaller and rapid expansions and contractions, also known as ringing. The combined mode of a laser pulse given together and synchronized with ultrasound is shown in FIG. 6 that depicts oscillation of membrane affected by ultrasound and shock wave from growing and collapsing vapor bubble around nanoparticle subjected to laser pulse. As in the experiment above, the membrane diameter is 50 nm, the nanoparticle diameter is 40 nm, the distance between the particle center and the membrane is 1,000 nm, the ultrasound acoustic pressure is 1.6 bar, and the ultrasound frequency is 10 MHz. As depicted in FIG. 6 the first dominant expansion/deviation peak is magnified from H=0.25 for laser only and about the same value for ultrasound only, see for example FIG. 4, to H=0.4 for laser plus ultrasound as depicted in FIG. 6.

Reference is now made to FIGS. 7A-7B, which are graphs depicting evolution of the gauge pressure field and temperature around the chromophore (granule), when the granule diameter is 2 μm, the pulse duration is 20 ns, the laser beam intensity is 2.4 MW/cm$^2$, and the absorption efficiency is 0.67. Reference is also made to FIGS. 7C-7D, which are graphs depicting evolution of the gauge pressure field and temperature around the granule, when the granule diameter is 2 μm, the pulse duration is 20 ns, the laser beam intensity is 2.4 MW/cm$^2$, and the absorption efficiency is 1.33.

If a spherical granules in an eye pigmented epithelium. Consider eye spherical pigmented granule of diameter 2 μm, absorption efficiency $K_{ab}$=1.34 and 0.67, see Pustovalov, V. K. and Horunzhiil A. Thermal processes during the interaction of optical radiation pulses with heterogeneous laminated biotissues. Int. J. Heat Mass Transfer, v. 33 (5), pp. 771-783, 1990, which is incorporated herein by reference, subjected to a laser beam of intensity 2.4 MW/cm$^2$ and the pulse duration 20 ns. This laser intensity equals to the minimal intensity that induces reversible damage in the to retina, see King R. G., Jr. and Geeraets W. J. The effect of Q-switched ruby laser on retinal pigment epithelium in vitro. ActaOphthalmalogica, vol. 46, 1968, which is incorporated herein by reference. It can be seen in FIGS. 7A-7D that a more drastic temperature and pressure rise occur at immediate vicinity of the granule. Pressure rise and temperature elevation propagate away from the granule and as demonstrated in FIGS. 8 and 9, a pressure rise of 1 bar reaches a double distance compared to a temperature elevation of 1 C. It should be noted that FIGS. 8 and 9 depict evolution of isobar (1 and 5 bar gauge respectively)

and isotherm (1° C. and 5° C. over initial temperature respectively) when the granule diameter is 2 μm, the pulse duration is 20 ns, the laser beam intensity is 2.4 MW/cm$^2$ and the absorption efficiency is 1.33. A cell and its bilayer membranes placed at a distance of 30 micrometer, for example from the granule, undergo a mechanical stimulation by the heated granule while the temperature rise is negligible at such a distance. This allows planning a mechanical (pressure) stimulation of cells by an optoacoustic heating of a granule without the cell being heated at 4 MW/cm$^2$ and the absorption efficiency is 0.67.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system of applying a nondestructive mechanical force on one or more cells in aqueous environment by generating heat generated acoustic pressure pulses, comprising:
    a computing unit adapted to provide an energy transmission pattern; and
    an interface which instructs according to said energy transmission pattern the radiating of a target area in an aqueous environment with a light energy to induce the forming of a plurality of heat generated acoustic pressure pulses that apply a desired nondestructive mechanical force on a cell membrane of at least one cell in proximity to said target area;
    wherein said desired nondestructive mechanical force is calculated so as to induce at least one of a periodic inflation and a periodic deflation of an intramembrane space of said cell membrane.

2. The system of claim 1, wherein said interface synchronizes the transmission of said light energy with acoustic energy to form said plurality of heat generated acoustic pressure pulses.

3. A computerized method of calculating instructions to at least one energy source, comprising:
    receiving instructions defining a desired nondestructive mechanical force to apply on at least one cell in an aqueous environment in proximity to a target area in said aqueous environment;
    receiving target information defining at least one characteristic said at least one cell;
    providing, using a processor, an energy transmission pattern to apply said desired nondestructive mechanical force on a cell membrane of said at least one cell by forming an heat generated acoustic pressure pulse in said target area; and
    outputting instructions to instruct at least one ultrasound radiation source and at least one focused light source to radiate said target area according to said energy transmission pattern;
    wherein said desired nondestructive mechanical force is calculated so as to induce at least one of a periodic inflation and a periodic deflation of an intramembrane space of said cell membrane.

4. The method of claim 3, wherein said target information comprises data pertaining to at least one characteristic of at least one chromophore in said target area.

5. The method of claim 3, wherein said energy transmission pattern is calculated according to a heat balance equation calculated for at least one chromophore in said target area.

6. The method of claim 3, wherein the wavelength of light emitted by said at least one focused light source is adapted to the light absorption wavelength of at least one chromophore in said target area.

7. A computer readable medium comprising computer executable instructions adapted to perform the method of claim 3.

8. The method of claim 3, wherein said aqueous environment is in a human body tissue.

9. The method of claim 3, further comprises an input unit adapted to receive target information defining at least one characteristic said at least one cell; wherein said energy transmission pattern is calculated according to said at least one characteristic.

* * * * *